United States Patent [19]

Swanepoel et al.

[11] Patent Number: 5,611,896
[45] Date of Patent: Mar. 18, 1997

[54] PRODUCTION OF FLUOROCARBON COMPOUNDS

[75] Inventors: Jacobus Swanepoel; Ruan Lombaard, both of Pretoria, South Africa

[73] Assignee: Atomic Energy Corporation of S. Africa Limited, Pelindaba, South Africa

[21] Appl. No.: 323,073

[22] Filed: Oct. 13, 1994

[30] Foreign Application Priority Data

Oct. 14, 1993 [ZA] South Africa ............... 93/7644

[51] Int. Cl.$^6$ ................................. C07C 17/00
[52] U.S. Cl. ............... 204/169; 422/186.22; 422/186.25; 422/906
[58] Field of Search ................ 204/164, 169; 422/186.04, 186.23, 186.25, 906

[56] References Cited

U.S. PATENT DOCUMENTS

| | | | |
|---|---|---|---|
| 2,732,411 | 1/1956 | Farlow et al. | 260/653 |
| 2,785,119 | 3/1957 | Cook et al. | 204/169 |
| 2,852,574 | 9/1958 | Denison et al. | 260/653 |
| 2,924,625 | 2/1960 | Forshey | 260/653 |
| 3,033,767 | 5/1962 | Olstowski et al. | 204/62 |
| 3,081,245 | 3/1963 | Farlow | 204/169 |
| 3,147,998 | 9/1972 | Tsantrizos | 219/121.5 |
| 3,904,501 | 9/1975 | Lagow et al. | 204/164 |
| 4,128,589 | 12/1978 | Pastor et al. | 260/653 |
| 4,973,773 | 11/1990 | Malone | 570/155 |
| 5,207,999 | 5/1993 | Burk et al. | 423/258 |

FOREIGN PATENT DOCUMENTS

| | | |
|---|---|---|
| 0515975 | 12/1992 | European Pat. Off. . |
| 911323 | 2/1991 | South Africa . |
| 1278495 | 6/1972 | United Kingdom . |

OTHER PUBLICATIONS

BR. Bronfin, "Flourine reactions in plasma", The Application of Plasmas to Chemical Processing edited by R.F. Baddour and R.S. Timmins, The Mit Press, Mass. Institute of Technology, Mass, and London, England (1967), pp. 157–200, no month available.

J.F. Brilhac et al., "Dimensionless relationships to calculate are characteristics in a vortex DC plasma torch", Journal of High Temperature Chemical Processes, Colloque, supplement Au No. 3, vol. 1, (Sep. 1992) 557–562.

Primary Examiner—Kathryn Gorgos
Assistant Examiner—Kishor Mayekar
Attorney, Agent, or Firm—Ladas & Parry

[57] ABSTRACT

The invention provides a method and installation for the production of a desired fluorocarbon compound, which includes the steps of providing a high temperature zone; and feeding at least one input material into the high temperature zone to generate a body of hot gas including fluorine-containing species and carbon-containing species. The molar C:F ratio in the body of hot gas is controlled at a selected value between about 0.4 and 2; and the specific enthalpy of the body of hot gas is controlled between about 1 kWh/kg and about 10 kWh/kg for a time interval, so that a reactive thermal gaseous mixture forms, containing reactive species including reactive fluorine-containing precursors and reactive carbon-containing precursors. Thereafter the reactive thermal mixture is cooled at a cooling rate and to a cooling temperature selected to produce an end product including the desired fluorocarbon compound. The input material is typically a $C_1$–$C_{10}$ perfluorinated carbon compound of the general formula $C_nF_m$ in which $0<n\leq 10$, and $m=2n$, $2n+2$, or $2n-2$ where $n>1$, for example a gaseous fluorocarbon such as tetrafluoromethane ($CF_4$).

24 Claims, 13 Drawing Sheets

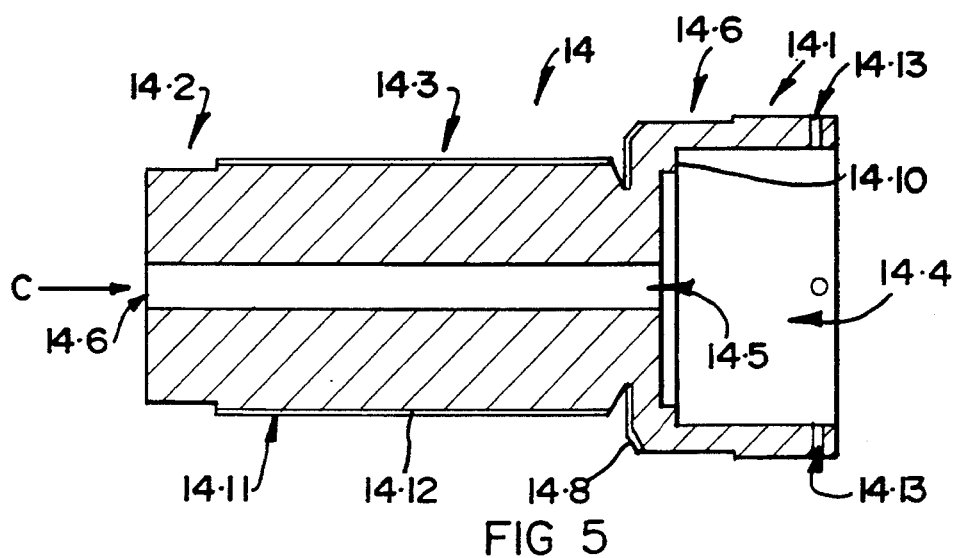
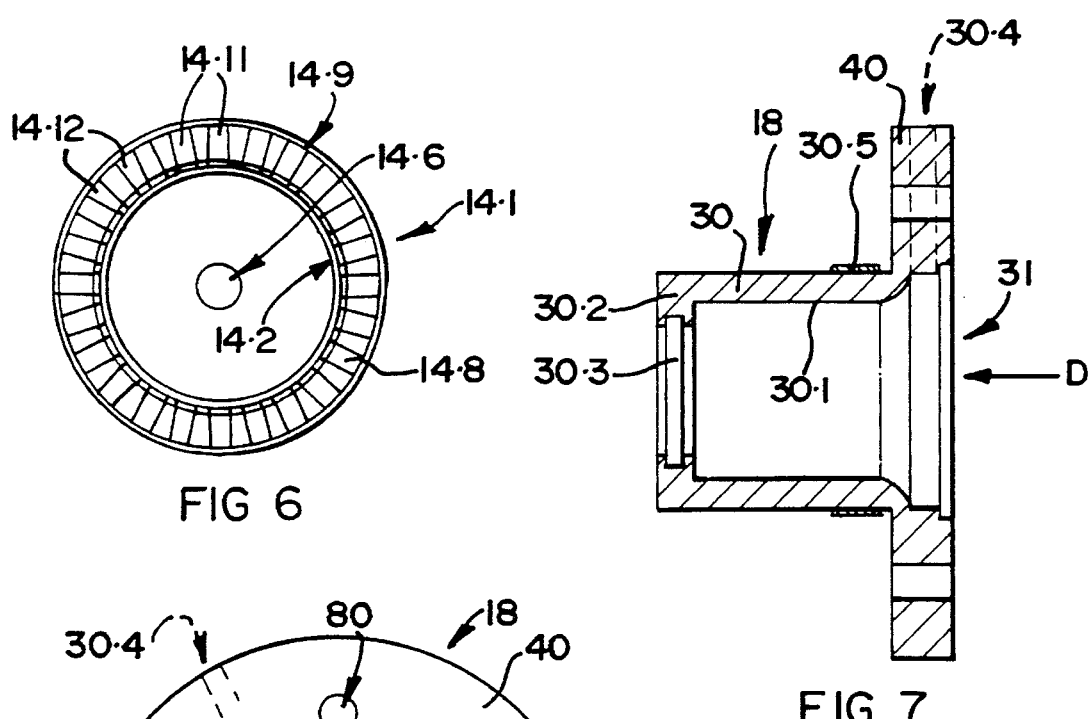
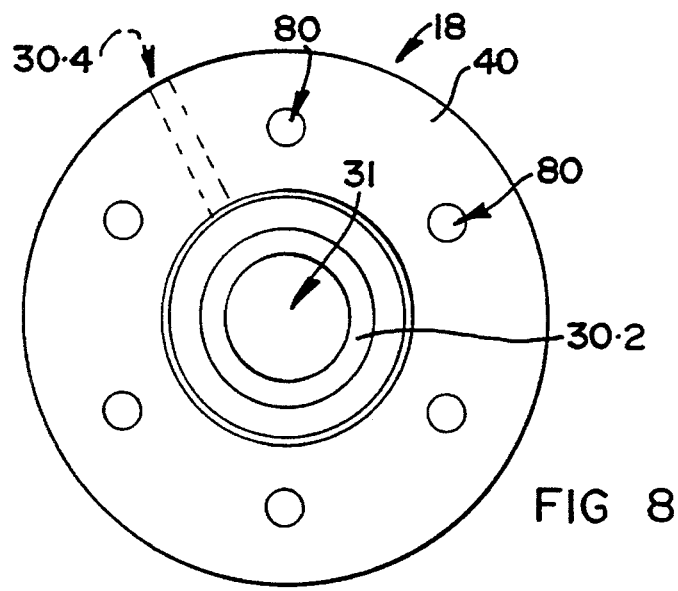

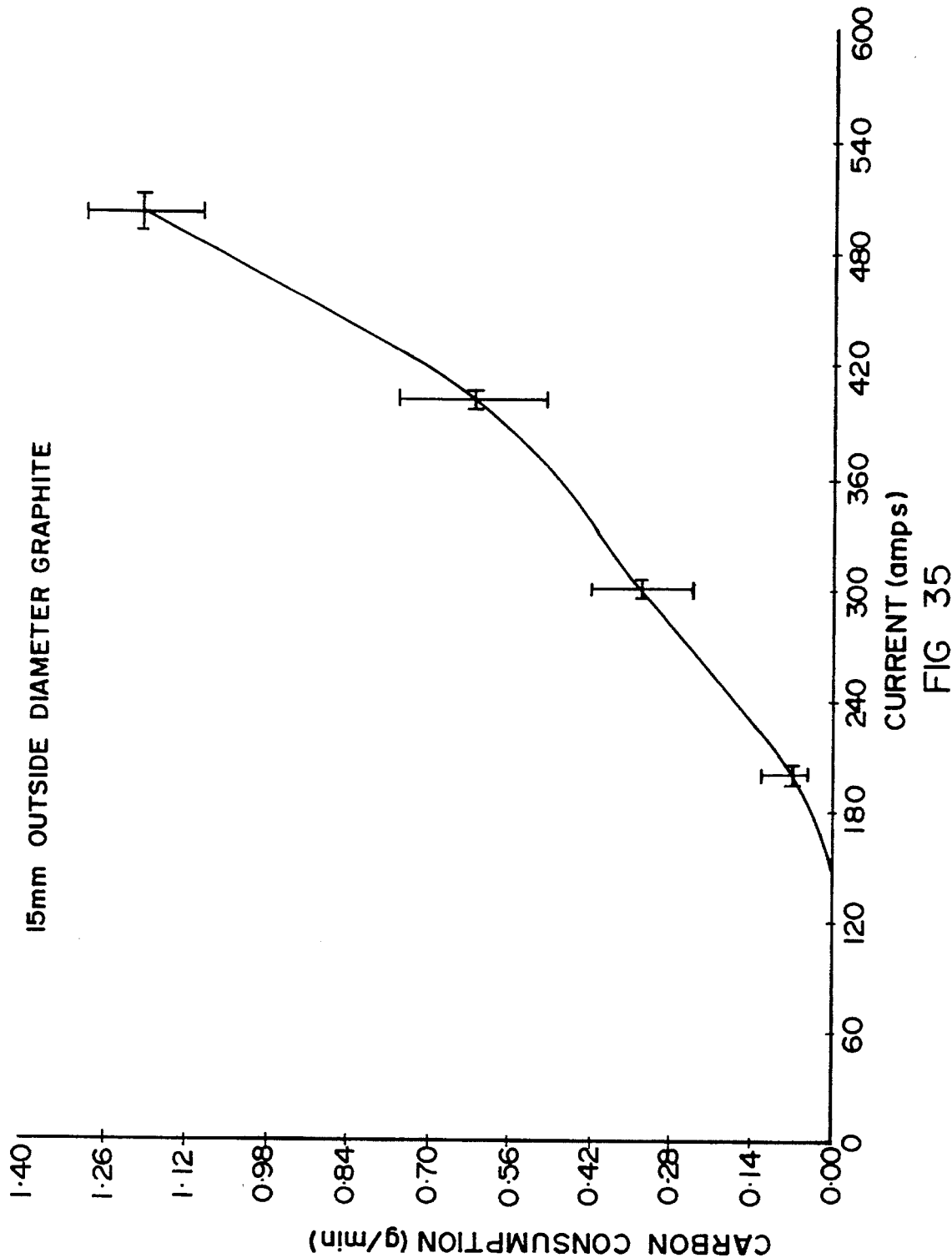

5,611,896

PRODUCTION OF FLUOROCARBON COMPOUNDS

FIELD OF THE INVENTION

THIS INVENTION relates to a method for the production of fluorocarbon compounds and to an installation and apparatus for the production of fluorocarbon compounds. More particularly, the invention relates to a method and to an installation and apparatus suitable for the continuous selective production of desired fluorocarbon compounds with minimal effluent production.

According to one aspect of the invention there is provided a method for the production of a desired fluorocarbon compound, which includes the steps of:

providing a high temperature zone;

feeding at least one input material into the high temperature zone with which to generate a body of hot gas including fluorine-containing species and carbon-containing species;

controlling the molar C:F ratio in the body of hot gas at a selected value between about 0.4 and 2;

controlling the specific enthalpy of the body of hot gas between about 1 kWh/kg and about 10 kWh/kg for a time interval to form a reactive thermal gaseous mixture containing reactive species including reactive fluorine-containing precursors and reactive carbon-containing precursors; and cooling the reactive thermal mixture at a cooling rate and to a cooling temperature selected to produce an end product including the desired fluorocarbon compound.

The C:F ratio in the body of hot gas will typically be selected to permit optimal production of the said precursors with optimal utilisation of energy.

Unless otherwise stated, the specific enthalpy indicated herein pertains to the thermal gaseous mixture, and reflects the value per kg of thermal gaseous mixture.

The input material may be an input gas stream and may include at least one fluorocarbon compound. Thus, the input material may include one or more fluorocarbon compounds selected to provide the desired molar C:F ratio in the body of hot gas, to enable the desired fluorocarbon end product to be produced. The fluorocarbon compound may be a short chain, typically $C_1$–$C_{10}$ perfluorinated carbon compound of the general formula $C_nF_m$ in which $0 < n \leq 10$, and $m = 2n$, $2n+2$, or $2n-2$ where $n > 1$, for example a gaseous fluorocarbon such as difluoroethyne ($C_2F_2$), tetrafluoroethylene ($C_2F_4$, TFE), hexafluoroethane ($C_2F_6$), hexafluoropropene ($C_3F_6$), octafluoropropane ($C_3F_8$), tetrafluoromethane ($CF_4$), or octafluorobutene ($C_4F_8$), or decafluorobutane ($C_4F_{10}$).

The desired fluorocarbon compounds to be produced by the method of the invention are typically $C_1$–$C_4$ fluorocarbons, such as tetrafluoroethylene ($C_2F_4$, TFE), hexafluoroethane ($C_2F_6$), hexafluoropropene ($C_3F_6$), octafluoropropane ($C_3F_8$), and tetrafluoromethane ($CF_4$, carbontetrafluoride).

It will be observed that some of the fluorocarbon compounds specifically mentioned as desired fluorocarbon end products, are the same compounds mentioned as possible input fluorocarbons. The invention thus envisages providing a method for efficiently converting an available but undesired fluorocarbon to another desired fluorocarbon compound; and a method of converting a mixture of fluorocarbon compounds to one or more purified desired fluorocarbon compounds.

According to a further feature of the invention, the method may include the further step of:

introducing under controlled enthalpy conditions a particulate carbon-containing substance into the body of hot gas to form in the reactive thermal gaseous mixture reactive precursors derived from the carbon-containing substance. Where the input material contains a fluorocarbon compound, the reactive precursors may thus be derived from the fluorocarbon compound and from the particulate carbon-containing substance.

The method may accordingly include the steps of:

providing a high temperature zone;

directing an input gas stream containing at least one fluorocarbon compound into the high temperature zone to generate a body of hot gas;

introducing under controlled enthalpy conditions a particulate carbon-containing substance into the body of hot gas to form a reactive thermal mixture having a molar C:F ratio between about 0.2 and 4 and a specific enthalpy between about 1 kWh/kg and 10 kWh/kg;

controlling the said specific enthalpy for a time interval to cause a reactive thermal gaseous mixture to be formed, said mixture containing reactive species including desired fluorine-containing and carbon-containing precursors derived from the at least one fluorocarbon compound and the particulate carbon-containing substance; and cooling the reactive thermal mixture in a manner to produce a product mixture containing the at least one desired fluorocarbon compound.

The body of hot gas in the high temperature zone may be provided by generating a plasma with the said input gas, eg by generating an electrical arc in the said high temperature zone between at least one pair of electrodes. The electrodes may be substantially non-consumable electrodes, as hereinafter defined.

The reactive species formed in the body of hot gas will depend on the composition of the input gas stream, the nature of the particulate carbon-containing substance and other factors. Furthermore, certain reactive species may form in the body of hot gas even prior to the introduction of the particulate carbon-containing substance, and further reactive species may form after introduction of the said carbon-containing substance. These reactive species will be described in more detail further below. The reactive species include certain desired precursors which, upon further reaction under suitable conditions of rapid cooling to selected reaction temperatures, will yield the desired fluorocarbon product(s).

As will be explained in more detail further below, the manner in which the reactive thermal mixture, containing amongst the reactive species the desired precursors, is cooled will determine the end fluorocarbon product(s). Accordingly, the cooling step preferably has a cooling rate, a range of cooled temperatures, and a time period for which the cooled thermal mixture is maintained at the range of cooled temperatures all of which are selected to determine the nature of the at least one desired fluorocarbon compound which is produced as an end product.

SUMMARY

The particulate carbon-containing substance may be introduced into the body of hot gas, e.g., the thermal plasma, in such a manner and under such enthalpy conditions as to form a reactive thermal mixture containing reactive species including desired precursors and preferably having a specific enthalpy of not less than about 3 kWh/kg. The particulate carbon-containing substance may be preheated prior to being introduced into the body of hot gas. The feed rate of the particulate carbon-containing substance and its preheated temperature may thus be controlled to provide a reactive thermal mixture in which the carbon-containing particles reach temperatures of between about 2000 K. and 3000 K.

The particulate carbon-containing substance may be introduced directly into the body of hot gas in the high temperature zone, or it may be introduced into a mixing zone for admixture with the body of hot gas emanating from the high temperature zone.

Thus, the method may include the steps of:

providing a high temperature zone by providing an arc between substantially non-consumable electrodes, and a mixing zone in the vicinity of the high temperature zone;

feeding an input gas stream containing at least one fluorocarbon substance into the high temperature zone and generating a thermal plasma in the said zone containing fluorine-containing species and carbon-containing species;

controlling the molar C:F ratio in the thermal plasma at a selected value between about 0.4 and 2;

controlling in the said high temperature zone the specific enthalpy of the thermal plasma between about 1 kWh/kg and about 10 kWh/kg;

introducing a particulate carbon-containing substance into the mixing zone to mix with the thermal plasma while maintaining the aforesaid C:F ratio to form a reactive thermal mixture in which the carbon-containing particles reach temperatures of between about 2000 K. and 3000 K., said reactive thermal mixture containing reactive species including reactive fluorine-containing precursors and reactive carbon-containing precursors and having a specific enthalpy of not less than about 3 kWh/kg;

maintaining the reactive thermal mixture at the aforesaid conditions for a time interval; and rapidly cooling the reactive thermal mixture containing the precursors in a cooling zone in a manner to produce a product mixture containing at least one desired fluorocarbon compound.

The mixing zone into which the particulate carbon-containing substance may be introduced may form part of the high temperature zone, or may be immediately adjacent the high temperature zone. In a preferred embodiment, the high temperature zone may be the zone in and around, and in the immediate vicinity of, the arc of a plasma burner, and the mixing zone may be at the exit from the burner, ie in the area of the tail flame of the burner.

The invention is based on the premise that fluorocarbons such as tetrafluoroethylene ($C_2F_4$, TFE), tetrafluoromethane ($CF_4$), hexafluoroethane ($C_2F_6$) and hexafluoropropene ($C_3F_6$) can be produced by heating a fluorocarbon substance, preferably in the presence of carbon, to create a body of hot gas with a controlled C:F ratio and a specific enthalpy of between about 1 kWh/kg and about 10 kWh/kg, and rapidly quenching the reaction mixture to a temperature below about 800 K. The high enthalpies required for the reaction may generally be achieved by processes such as resistive heating using graphite resistors, inductive heating of graphite using radio frequencies, inductively or capacitively coupled plasma generation, plasma generation by low frequency alternating current or plasma generation by direct current with the use of different electrode systems, e.g., low consumption intensely cooled carbon electrodes, or cooled non-carbon electrodes, or intensely cooled non-carbon/carbon electrodes.

Thus, the objective of the invention is for a high temperature plasma to be formed which contains reactive species some of which will form, with carbon, the desired reactive precursors, which precursors in the presence of carbon during and after quenching will produce the desired fluorocarbon products.

Where the input gas with which the high temperature plasma is generated, includes a fluorocarbon compound, the following reactive species may be formed, namely $CF_3$, $CF_2$, CF, F, C and their ions.

On mixing the plasma gas with carbon particles, the following reactive species may be formed, namely C (gas), C (sol), $C^+$ (ion), $C_2$ (gas), $C_2F_2$ (gas), $C_2F_4$, $C_2F_6$, $C_3$ (gas), CF (gas), $CF^+$ (ion), $CF_2$ (gas), $CF_3$ (gas), $CF_4$ (gas), F (gas), $F^-$ (ion), and e (electron). Of these reactive species, the following are the desired precursors for $C_2F_4$ (TFE) production, namely $C_2F_2$, $CF_2$, $CF_3$, CF and F. Accordingly, the enthalpy of the body of hot gas, the C:F ratio in the body of hot gas, and the prevalent pressure may be controlled to promote the predominance in the reactive thermal mixture of these reactive precursors.

In experimental procedures the process has been carried out at pressures which range from 0.01 bar to 1.0 bar using $CF_4$ as the input fluorocarbon compound and with direct current (DC) plasma devices with uncooled carbon electrodes and current fluxes which range between 40 and 120 $A/cm^2$. It was found that such carbon electrodes sublime when current above a certain level is passed through the electrodes under certain conditions of temperature and pressure, for example when current in excess of 100 $A/cm^2$ is passed through the electrodes at atmospheric pressure and at temperatures of about 4000 K. (This is illustrated in and will be further explained with reference to FIG. 35.) It was further determined that the current level at which sublimation of the carbon electrodes occurs decreases with decreasing pressure, so that a measurable amount of carbon is sublimed at a current above about 80 $A/cm^2$ and at pressures of about 0.01–0.1 bar; and that the sublimation temperature of the carbon likewise decreases with decreasing pressure, so that the sublimation temperature drops to about 3000 K. at pressures of about 0.01–0.1 bar. (This will be illustrated in and further explained with reference to FIGS. 27–30.)

It is believed that in the aforesaid experimental procedures using $CF_4$ as the fluorocarbon starting material and using direct current plasma generation with uncooled carbon electrodes, the sublimed carbon from the electrodes provides sufficient carbon required for an appreciable yield (about 80%) of TFE, thus causing the carbon electrodes to be consumed rapidly. It is evident, therefore, that such a procedure does not readily lend itself to continuous operation.

The experimental work thus showed that the use of plasma devices with uncooled carbon electrodes was unpractical, since the electrodes were consumed, and it has not been possible up to now to run the production process for more than a few minutes.

The Applicant has found that plasma devices using substantially non-consumable electrodes can be used successfully to run the process for substantially longer periods, i.e., up to several hours. An important aspect that emerged from the work done by the Applicant, demonstrates the need for the electrodes to be made of materials showing good resistance to chemical fluorine corrosion at elevated operational temperatures, eg temperatures up to about 1300 K., and coupled therewith, the need for the electrodes to be cooled and even intensely cooled, to temperatures below about 1300 K. and in the case of graphite, to below about 800 K.

By substantially non-consumable electrodes is meant electrodes which can operate for more than a few minutes and up to several hours without being substantially consumed, i.e., without undergoing substantial deterioration and/or erosion. Typically, cooled or even intensely cooled metal electrodes such as copper or copper alloy electrodes may be used, which may have inserts of suitable refractory materials, such as carbon or graphite inserts. The inserts may, instead, be of doped graphite or a high temperature metal alloy comprising tungsten, thoriated tungsten, other doped tungsten alloys, zirconium, hafnium, hafnium carbide, tantalum, tantalum carbide or any other suitable high temperature material. The electrodes are described in further detail below. The electrodes may form part of a plasma generating device, such as a high voltage DC plasma burner. In what follows, the method of the invention will be described with reference to the use of high voltage DC plasma burners as the means for generating a high temperature plasma. More than one, preferably three, such plasma burners may conveniently be provided, the plasma burners having exit ports where tail flames will be formed, in a conventional manner, and the burners being arranged to extend into a mixing chamber forming part of a production installation.

As indicated above, the electrodes are preferably non-consumable cooled metal electrodes, in some cases having inserts such as of graphite. One reason why such electrodes are preferred, apart from their relative longevity, is that no or only little erosion of the electrodes occurs, so that no or only little erosion products are formed, and blockage of the burner exit ports is avoided. In experimental work, using consumable carbon electrodes, it was found that the carbon sublimed, and that solidification of the sublimed carbon took place in the cooler exit port areas of the burner. The solidified carbon formed a hard mass which caused blockage of the exit ports of the burner, as well as fouling and blockage of the quenching means provided to effect rapid cooling of the reactive mixture, as will be described in more detail further below. Such carbon deposition and solidification will thus impede and/or impair the continuous running of the process.

With non-consumable electrodes, as envisaged by the invention, e.g., cooled copper or copper alloy electrodes having graphite inserts, it has become possible to run the process for several hours, namely periods in excess of about 8 hours and up to about 3 days. This feature of the invention creates the possibility of providing a viable commercial production process for producing the fluorocarbon products as described herein, particularly TFE, in a manner permitting recycling of byproducts with minimal waste effluent formation.

Where a plurality, for example three plasma burners are used, they may be arranged to extend into a mixing zone, e.g., in the form of a mixing chamber, in such a manner that, in use, their tail flames will extend into the mixing chamber and so that an extended high temperature zone may be established, surrounded by a mixing zone with a temperature only slightly lower than that in the high temperature zone.

The fluorocarbon compound in the input gas stream may be a compound such as $CF_4$ or $C_2F_6$, or mixtures thereof, or it may be comprised of or include dilute mixtures of $F_2$ gas. In practice, the preferred enthalpy level may have to be adjusted depending on the composition of the input gas, to ensure optimal operational and production efficiency.

The particulate carbon-containing substance may be introduced into the body of hot gas in fine particulate form, e.g., having a particle size from about $10^{-3}$ mm to about 0.3 mm. As already indicated, the feed rate is preferably regulated to provide a molar C:F ratio in the reactive thermal mixture of between about 0.4 and 2, and so that the carbon particles in the thermal mixture will reach temperatures of between about 2000 K. and 3000 K. The specific enthalpy of the reactive thermal mixture is preferably maintained at not less than about 3 kWh/kg. It will be evident that the enthalpy (and thus the temperature) of the reactive thermal mixture will depend inter alia on the temperature and the quantity of the carbon particles added.

The particulate carbon-containing substance may be fed into the mixing zone from a hopper, and may be preheated in the hopper or between the hopper and the mixing zone, before being fed into the mixing zone. The particulate carbon-containing substance may be introduced into the mixing zone at a rate of as low as 0.1 g/min for small scale operations, which rate may be increased for commercial scale operations, to maintain the desired C:F molar ratio. The substance may be particulate carbon. The carbon should preferably be substantially pure, although it may contain a small proportion of ash. In particular, the hydrogen, silicon and sulphur content of the carbon should be as low as possible. The carbon should preferably be substantially free of hydrogen, silicon and sulphur.

The mixing zone will typically be at a pressure of about 0.01–1.0 bar. In the mixing zone a reactive thermal mixture is formed as a result of the reaction of the carbon with the reactive species in the plasma, said reactive thermal mixture containing desired reactive fluorine-containing and carbon-containing precursors. When the reactive thermal mixture is cooled rapidly, e.g., quenched, and is allowed to react for a suitable period at the cooled temperature, the desired fluorocarbon end products are formed. The rate of cooling, as well as the temperature range after cooling and the reaction time at the cooled temperature range will determine the end products formed as well as the yields, as will be described in more detail below.

The particulate carbon may, instead or in addition, be introduced into the high temperature zone, e.g., into the arc area between the electrodes of the burner, provided the problems of sublimation and subsequent solidification and fouling referred to above can be successfully addressed. The carbon is preferably introduced into the tail flame of the plasma burner(s) which may be directed into the mixing zone. To ensure optimum enthalpy conditions in the mixing zone with minimal cooling of the plasma flame, the carbon particles may, as indicated above, be preheated.

The particulate carbon-containing substance may instead be or may include particulate polytetrafluoroethylene (PTFE). The method may thus include the further step of introducing into the high temperature zone, or into the mixing zone, polytetrafluorethylene (PTFE), or mixtures of PTFE and carbon. Where the further carbon-containing substance is PTFE, it is preferably fed into the mixing zone. It will be evident that waste supplies of PTFE may be utilised in this manner, so that PTFE wastes may be recycled and reprocessed.

The method may, still further, include the step of introducing fluorine gas into the high temperature zone or into the mixing zone. Thus, the input gas stream may include fluorine gas, and the fluorine gas may for example be present in an amount between about 5 and 30 mol % of the input gas.

The enthalpy condition of the reactive thermal mixture is typically maintained at a specific enthalpy above about 1 kWh/kg, and preferably not less than about 3 kWh/kg. As indicated above, the carbon particles react with the reactive species formed in the high temperature zone, while heat is transferred to the carbon particles, to form inter alia desired reactive fluorine-containing and carbon-containing precursors in the reactive thermal mixture such as $CF_2$, $C_2F_2$, $CF_3$, CF and F which, on cooling and further reacting, form fluorocarbon compounds such as TFE, $C_2F_6$, $C_3F_6$, $C_3F_8$ and $CF_4$. By controlling the rate of cooling or quenching, the effective range of quench temperatures, and the time period for which the reactive mixture remains within the particular range of temperatures after quenching, it is possible to increase the yield of one or other of the above products. For example, to obtain the maximum yield of TFE it is preferable to cool the reactive precursors to below about 800 K. in less than about 0.05 seconds. It is also possible, for example, to isolate the reactive compound $C_2F_2$ by cooling the reactive precursors rapidly to below about 100 K. Generally, the cooling of the reactive thermal mixture will take place within a selected cooling period and to a selected range of cooled temperatures, and the thermal mixture will be maintained within the selected range of cooled temperatures for a selected period of time, and all of these parameters will be selected to determine the desired fluorocarbon compound(s) produced in the end product.

To enhance the yield of $C_2F_6$ longer cooling times, of the order of 0.05–3 seconds can be used. On the other hand if the cooling is to a temperature above 800 K., for example a temperature between about 1000 K. and 1200 K., the yield of $C_3F_6$ can be maximised. If the reactive precursors are not rapidly cooled, the product is primarily $CF_4$. The production of $CF_4$ on a large scale can be achieved if fluorine is fed into the mixing zone during the production process.

The cooling step may be achieved in accordance with conventional techniques, e.g., by using a cold wall heat exchanger or a single- or multi-tube heat exchanger, or by cold fluid mixing, or by combinations of the foregoing, or in any other suitable manner. The heat exchanger used in the cooling step should preferably be of a type which allows cooling of the reactive precursors from about 2500 K. to below about 800 K. in a very short time, typically less than about 0.1 seconds. Where cooling or quenching is achieved by cold gas mixing, the cold gas may be a fluorocarbon gas or a suitable inert gas.

Thus, the method may include the step of rapidly cooling the reactive precursors in the cooling zone to a selected temperature between about 100 K. and about 1200 K. at a rate of between about 500 and $10^8$ K/s, and allowing the precursors to react at that selected temperature for a suitable time interval, depending on the desired end product.

For example, the invention provides a method for producing TFE by cooling the reactive precursors to below about 800 K. in less than 0.05 seconds and allowing a suitable reaction time, e.g., of about 0.01 seconds. It also provides a method for producing $C_2F_6$ by cooling the reactive precursors to below about 800 K. in about 0,05–3 seconds and allowing a suitable reaction time; or for producing $C_3F_6$ by cooling the reactive precursors to between about 800 K. and about 1000 K. in about 0.05–3 seconds and allowing a suitable reaction time. The invention further provides a method for producing $C_2F_2$ by rapidly quenching the reactive precursors to below about 100 K. and allowing a suitable reaction time; or for producing $CF_4$ by allowing the precursors to react without quenching.

For example, when cold wall tubular heat exchangers are used, optimum TFE yield may be obtained by the correct choice of heat exchanger parameters such as tube diameter and length, temperature of cooling fluid, mass flux of the process stream, etc. Generally, quench periods and the aforesaid cooled temperature may in practice be adjusted by varying the mass flux through the heat exchanger and the length of the heat exchanger. Preferably, a fixed wall heat exchanger may be used, i.e., heat exchanger which operates without the intermixing of a cooling fluid with the thermal mixture, and in which a heat conductive separating wall is provided between the cooling fluid and the thermal mixture. This has the advantage of avoiding subsequent large scale separation procedures.

The method may accordingly include the further step of isolating at least one desired fluorocarbon compound from the product mixture. Other components in the product mixture may be separated and recycled.

The process may be carried out at an absolute pressure of about 0.01–1.0 bar.

As indicated above, the rate of introduction of the particulate carbon and/or polytetrafluoroethylene (PTFE) and/or fluorine-containing compound into the plasma should preferably be such as to regulate the C:F ratio in the plasma at a level between about 0.4 and 2.0 and preferably at about 1. Like the carbon, the PTFE may be introduced in the form of a powder having a particle size from about $10^{-3}$ mm to 0.3 mm. Preferably the particle size is about $10^{-3}$ min.

The carbon and/or PTFE may be introduced into the mixing zone by means of a gravity feed mechanism, or by way of gas transfer, preferably using a portion of the input gas stream as a flow transfer means. In practice, the pressure in the carbon feed hopper may be reduced to a value below the selected optimal pressure, say to about $10^{-2}$ bar (absolute), and thereafter the pressure may be increased and set at the optimal level by introducing the fluorocarbon gas. As indicated above, the temperature of the carbon and/or PTFE particles may be adjusted prior to their introduction into the mixing zone, to enhance the achievement and control of the desired specific enthalpy, and to ensure optimum performance.

Since the reaction between fluorine and carbon is highly exothermic, it is possible to reduce the required energy input by the controlled introduction of fluorine into the mixing zone. Other methods may also be utilised to optimise energy input.

Thus, the method may include the step of introducing fluorine into the mixing zone. The fluorine may be introduced as a mixture with a fluorocarbon gas. The amount of fluorine in the mixture may be between about 5 and 30 mol %.

It is important, when fluorine is introduced into the system, to regulate the ratio between introduced fluorine, introduced carbon and input gas to maintain the ratio of C:F between about 0.4 to 2.0, preferably about 1, and the specific enthalpy of the mixture between about 1 kWh/kg and 10 kWh/kg, and preferably about 3 kWh/kg in the case of a fluorocarbon feed gas. The fluorine may, for example, be introduced into the tail flame of the plasma burner(s).

The product mixture may include unreacted carbon-containing particles. Thus the method may include a separation step for removing solid particles from the product mixture, e.g., by filtering the product mixture. The product mixture may, for example, be filtered through a high temperature filter such as a PTFE, a SiC or a metal filter. Naturally, any other method of separation suitable for removing a solid material from a gas stream may be used, such as cyclonic separation.

The method may include the step of recycling the carbon-containing particles removed in the separation step back to the hopper.

In practice, the method is preferably conducted in such a manner to minimise ingress of $N_2$ or $O_2$ or water vapour, which would result in the formation of unwanted and/or unstable products.

Compounds such as HF or $F_2$ may be removed from the product mixture before or after, but preferably after the gas-solid separation step. Thus the method may include the further step of passing the product through one or more chemical or cold traps to remove impurities such as HF or $F_2$. For example, the product may be passed through a trap containing carbon at a temperature typically of 700 K. to remove $F_2$, and a trap containing NaF to remove HF. The HF may, instead, be removed by cooling the product to liquify the HF. Instead, fluoride impurities may be removed by scrubbing with a dilute alkaline solution, preferably a KOH solution, to remove reactive fluorides from the gaseous product.

The method may include the further step of compressing the product gases. The product gases may be compressed to a pressure below about 20 bar, preferably about 10 bar which is high enough to allow distillation or membrane separation of the components of the product gases under safe conditions. The pressure should naturally be kept low enough to inhibit or prevent spontaneous polymerisation of unsaturated components of the product gases or the exothermic conversion of TFE to carbon and $CF_4$. The invention envisages the addition of an inhibitor during the compression and separation steps, to ensure safe operation.

Other purification procedures such as gas centrifugation may, instead or in addition, be used.

The product gas will typically be stored in limited volumes in pressurised tanks with the addition of a suitable inhibitor, or it may be transferred to other plants for further chemical transformations, such as polymerisation, to produce PTFE. Unwanted product fluorocarbon gases may be recycled for reuse in the input gas stream.

According to another aspect of the invention, there is provided an installation for the production of fluorocarbon compounds, the installation including a high temperature zone suitable for containing a body of hot gas;

heat generating means to create a high temperature in the high temperature zone, to convert an input material fed into the zone into a said body of hot gas including fluorine-containing species and carbon-containing species;

input material feed means for introducing an input material into the high temperature zone so that the input material is converted to a said body of hot gas;

a reaction zone suitable to permit the body of hot gas to form a reactive thermal gaseous mixture under controlled enthalpy conditions and with a controlled C:F ratio, said mixture containing reactive species including reactive fluorine-containing precursors and reactive carbon-containing precursors;

control means for controlling the specific enthalpy and the C:F ratio in the reactive thermal mixture; and cooling means for cooling the reactive thermal mixture in a controlled manner to produce an end product containing at least one desired fluorocarbon compound.

The installation may include further a mixing zone suitable for allowing the body of hot gas to mix with a particulate material to form a reactive thermal mixture; and particulate material introduction means for introducing under controlled enthalpy conditions a said particulate carbon-containing substance into the body of hot gas in the mixing zone to form a said reactive thermal mixture containing reactive species including reactive fluorine-containing precursors and reactive carbon-containing precursors.

The heat generating means is preferably capable of generating a plasma with the said input gas stream. The heat generating means may include at least one pair of substantially non-consumable electrodes, located in the high temperature zone for generating an electrical arc. The arc may be such as to heat the gas stream to create a plasma having a specific enthalpy between about 1 kWh/kg and about 10 kWh/kg, preferably not less than about 3 kWh/kg. As already indicated, the electrodes are preferably non-consumable electrodes.

By non-consumable electrodes is meant electrodes as described above which can operate for several hours without being substantially consumed or showing substantial deterioration and/or erosion.

The heat generating means may thus include at least one plasma burner having a pair of substantially non-consumable electrodes selected from the group consisting of copper, nickel, and copper/nickel alloy electrode, optionally with an insert of the group consisting of graphite and doped graphite; and in which cooling means is provided for cooling the electrodes to and maintaining them at a temperature below about 1300 K.

The mixing zone may form part of the high temperature zone or may be immediately adjacent the high temperature zone. In a preferred embodiment of the invention the installation may include at least one plasma burner provided with substantially non-consumable electrodes as herein described. The high temperature zone may be the zone in and around the arc generated between the electrodes of the plasma burner, and in the immediate vicinity of the arc. The mixing zone may be at an exit from the burner, ie in the area of the tail flame of the burner.

The installation may include a plurality, preferably three plasma burners and the mixing zone may be a mixing chamber, the burners being arranged to extend into the mixing chamber in such a manner that in use their tail flames extend into the mixing chamber, so that an extended high temperature zone may be established, surrounded by a mixing zone with a temperature only slightly lower than that in the high temperature zone.

The gas stream introduction means may be a vortex generator, forming a part of the plasma burner, and the input gas stream may be introduced into the high temperature zone via the vortex generator. The installation may further include a magnetic coil for generating a magnetic field around the high temperature zone to cause the plasma to spin.

The particulate material introduction means for introducing the particulate carbon-containing substance into the high temperature zone may be a hopper which may be designed to deliver particulate material having a particle size from about $10^{-3}$ mm to about 0.3 mm at a rate of as low as about 0.1 g/mm, to an increased rate as required by the operational parameters and so as to maintain a suitable C:F ratio as hereinbefore described. The hopper may be arranged to introduce the particulate material into the mixing chamber, e.g., into the tail flame of the plasma burner. It may, instead, be arranged to introduce the particulate material into the arc, although this is not preferred in view of the problems caused by sublimation and subsequent solidification of carbon masses, causing fouling and blockage, referred to hereinbefore.

The installation may, further, include heating means located between the hopper and the mixing zone for heating the particulate carbon-containing material before it enters the mixing zone. The installation may also be provided with a vacuum pump for evacuating the installation to a pressure of about 0.01–1.0 bar.

The installation may include a heat exchanger, such as a single- or multi-tube heat exchanger, or a cold fluid mixing system, or combinations of different heat exchange systems. The objective is to cool the reactive thermal mixture rapidly and to maintain the product mixture at the cooled temperature for a suitable period of time, to produce a product mixture containing one or more desired fluorocarbon products. The heat exchanger will preferably be of the type which will cool the reactive thermal mixture from about 2500 K. to below about 800 K. in a very short time, typically less than about 0.1 seconds, and to maintain the product mixture at that cooled temperature for a suitable time period.

The installation may, if desired, include fluorine introduction means for introducing fluorine into the tail flame of the plasma burner or into the mixing zone. Because of the highly exothermic nature of the reaction between fluorine and carbon, it is possible to reduce the required energy input into the system by the controlled introduction of fluorine into the mixing zone.

The installation may, further, include separation means for removing solid particles from the product mixture. For example the separation means may be a high temperature filter such as PTFE, a SiC or a metal filter. It may instead, be a cyclone separator. The installation may, further, include recycling means for recycling carbon removed in the separation step back to the hopper. The installation may also include one or more chemical or cold traps to remove impurities such as HF or $F_2$.

The installation may further include a compressor for compressing the product gases, and storage tanks for storing the product produced.

The invention extends also to a plasma burner suitable to be used as part of an installation according to the invention, for creating a body of hot gas in the form of a high temperature plasma as part of a production process for producing fluorocarbon compounds. The plasma is to be generated from an input gas stream including a fluorocarbon compound, and the generated plasma will accordingly contain reactive species including $CF_3$, $CF_2$, $C_2F_2$, CF, F, C and all their ions.

In view of the corrosive nature of some of these reactive species and the relatively high prevalent specific enthalpies (and temperatures), and in view further of the importance of maintaining certain preferred operational parameters in generating the plasma, as fully described herein, the invention provides a plasma burner (also referred to herein as a plasma torch) suitable to operate under these conditions.

According to the invention a plasma burner includes a pair of non-consumable electrodes (as herein defined) being a cathode and an anode and each having an operational end;

the anode being of resistant metal and of hollow configuration to define an open-ended internal anode cavity providing a tubular operational face extending from the operational end to an exit end;

the cathode being of resistant metal and having a graphite insert to define a button-type operational face at its operational end;

the cathode and anode being arranged in end-to-end relationship with their operational ends in spaced alignment to define between them a gap which together with the anode cavity defines an arc location for an arc to be generated when a potential difference is applied across the electrodes;

the electrodes being configured to provide flow lines for a cooling fluid to flow through or over them;

the electrodes being mounted in a housing comprised of a plurality of annular housing components dimensioned and shaped to nest together with the inclusion of suitable electrical insulation means, and being internally configured to define a mounting location for the electrodes;

at least one housing component incorporating flow passages for the introduction and evacuation of a cooling fluid;

at least one housing component incorporating flow passages for the introduction of an input gas stream in a manner to create a vortex within the arc location;

the arrangement being such that, in use, an arc may be generated in the arc location when a potential difference is applied across the electrodes, and a high temperature plasma may be generated with the input gas in a high temperature zone located within the arc location, to produce a reactive thermal plasma emanating at the exit end of the anode cavity.

According to a further feature, particulate material introduction means may be provided to introduce a particulate carbon-containing substance under controlled conditions of enthalpy into the reactive plasma emanating at the exit end of the anode cavity.

Further features of construction and operation will appear from the description contained herein, particularly the description with reference to the drawings.

BRIEF DESCRIPTION OF THE DRAWINGS

The invention will now be described, by way of example, with reference to the accompanying diagrammatic drawings, which are not all drawn to the same scale, and in which

FIG. 5 is a sectional side view of the anode of the plasma torch of FIG. 1;

FIG. 6 is an end view of the anode of FIG. 5 viewed in the direction of the arrow C in FIG. 5;

FIG. 7 is a sectional side view of the first housing component of the plasma torch of FIG. 1;

FIG. 8 is an end view of the housing component of FIG. 7, viewed in the direction of the arrow D in FIG. 7;

FIG. 35 is a graph depicting carbon consumption from a 15 mm graphite rod in grams per minute as a function of current in amps.

DESCRIPTION

Figure 1:
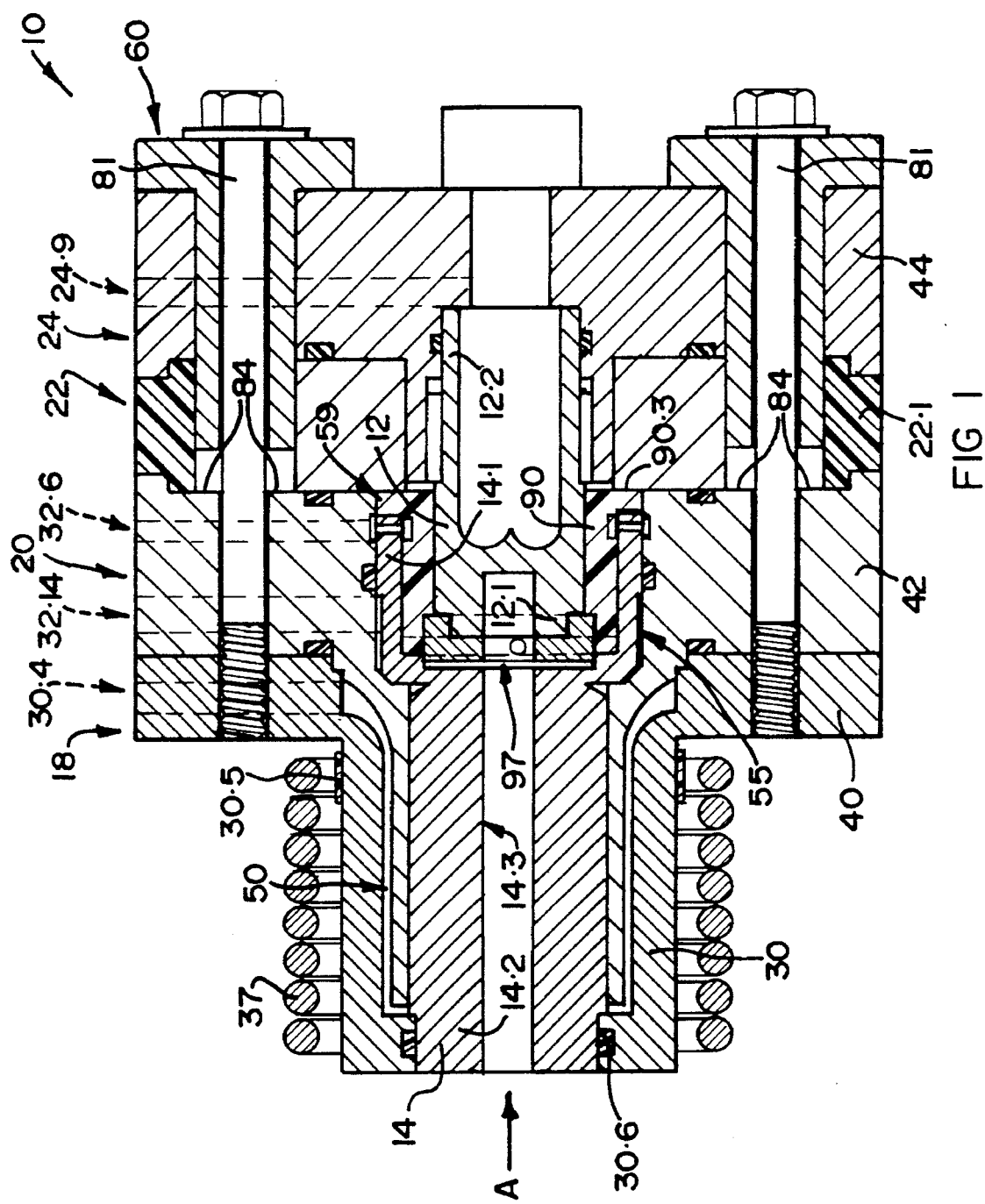
FIG. 1 is a sectional side view of a plasma torch suitable to be used to provide a reactive thermal mixture in accordance with the invention.
Figure 2:
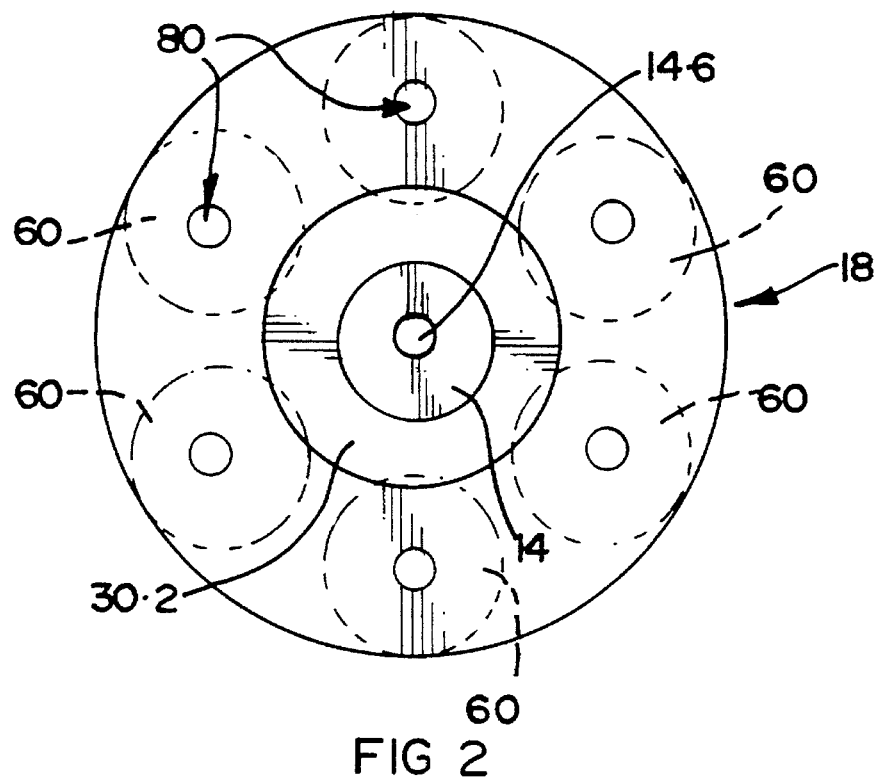
FIG. 2 is an end view of the plasma torch of FIG. 1, viewed in the direction of the arrow A in FIG. 1.

Referring to FIG. 1 reference numeral 10 generally indicates a plasma torch suitable to be used in a method for producing fluorocarbon compounds in accordance with the invention. The torch 10 includes a copper alloy cathode 12 and a copper alloy anode 14 mounted in a housing. The housing includes first, second and fourth annular conductive housing components 18, 20, 24 and a third annular insulating housing component or insulator 22, all of the components being secured in an abutting arrangement as can be seen in FIG. 1. The cathode 12 and the anode 14 are coaxially mounted in the housing. The cathode 12, which is described in further detail below, has an inner operational end 12.1 which is adjacent the anode 14 and an opposed outer end 12.2. The anode 14, which is also described in further detail below, is hollow and has an inner end portion 14.1 which is adjacent the cathode, an opposed outer end 14.2, and a cavity 14.3 which provides a tubular operational face. The operational end 12.1 of the cathode 12 is received in the end portion 14.1 of the anode 14 as can also be seen in FIG. 1.

Referring to FIGS. 1, and 7 to 11, the housing components 18 and 20 each consists of a hollow cylindrical body 30, 32 which is open at both ends and which defines passages 31, 33 respectively. Each component 18, 20 has a radially outwardly projecting disc shaped flange 40, 42, located at one of its ends. The components 18, 20 are made of stainless steel. The body 32 has a smaller diameter than the body 30 and is received inside the body 30 with clearance 50 as can be seen in FIG. 1.

Referring now in particular to FIGS. 7 and 8, the body 30 of the first housing component 18 has an inner surface 30.1 with a stepped inner cross-sectional profile as can be seen in FIG. 7. An annular rim 30.2 at the end of the body 30 remote from the flange 40 projects inwardly and is provided with an annular groove 30.3 to receive a seal 30.6 (see FIG. 1). In the plasma torch 10, the seal 30.6 abuts against an outer surface of the end portion 14.2 of the anode 14 which is slightly recessed, as can be seen more clearly in FIG. 1, and which is described in further detail below. A coil 37 for generating a magnetic field surrounds the body 30 (FIG. 1). The coil generates a magnetic field of 0.01–0.30 Tesla.

A water outlet conduit 30.4 extends radially outwardly through the flange 40 from the passage 31. The body 30 further has an outwardly directed screw threaded portion 30.5 next to the flange 40 for receiving a mounting flange as is described in further detail below.

Referring specifically to FIGS. 1 and 9 to 11, the body 32 of the second housing component 20 has an inner surface 32.13 and an outer surface 32.1 which outer surface, together with the inner surface 30.1 of the body 30 of the component 18, in the plasma torch 10, defines an annular cavity 50 (FIG. 1) around the body 32. The body 32 has an inner shoulder 32.3 which, in the plasma torch 10, abuts against the anode 14 (FIG. 1). A water inlet conduit 32.2 extends radially inwardly through the flange 42 to the passage 33 and a gas inlet conduit 32.6, next to the water inlet conduit 32.2, also extends radially inwardly to the passage 33. The flange 42 further has an annular ridge 32.7 and two annular grooves 32.8, adjacent the body 32 on either side of the flange 42 for receiving O-rings. The portion of the passage 33 defined by the flange 42, has an inner surface 32.4 with an annular groove 32.5 for receiving an O-ring, and an annular gas conduit groove 32.9 next to it.

A copper connector 32.10 with an opening 32.11 for attachment of an electrical cable (not shown) projects from the flange 42 for connecting the cable to the flange 42.

Referring to FIGS. 1, 5 and 6 the anode 14 has, as mentioned above, an outer end portion 14.2 and an inner end portion 14.1 which is cup-shaped and which defines a cylindrical opening 14.4. The portion 14.1 is provided, near to the opening 14.4, with four gas openings 14.13 for the introduction of gas via the gas inlet conduit 32.6 and the gas conduit groove 32.9. The opening 14.4 is separated by a shoulder 14.10 from a narrower axially oriented passage 14.5 which constitutes an anode cavity and connects the opening 14.4 to an opening 14.6 in the outer end portion 14.2. A part 14.6 of the external face of the cup-shaped portion 14.1 is recessed and has a cut away shoulder 14.8. The recessed portion 14.6 of the anode 14 and a portion of the inner surface 32.4 of the second housing component 20 together define, in the plasma torch 10, an annular cavity 55 (FIG. 1). The outer end portion 14.2 of the anode 14, as mentioned above, is recessed so that a central portion 14.3 appears slightly raised. The inner surface 32.13 of the component 20, in the plasma torch 10, abuts against the raised portion 14.3 of the anode 14 (FIG. 1). The anode is about 67 mm long and has a diameter of about 32 mm at its widest point.

Referring in particular to FIGS. 5 and 6, the raised portion 14.2 of the anode 14 and the cut away shoulder 14.8 are provided with longitudinal ridges 14.11 defining longitudinal grooves 14.12.

The cavities 50, 55, the inlet and outlet conduits 32.2, 30.4 and the grooves 14.12 constitute a flow path for cooling water to cool the anode, as can be seen in FIG. 1. The anode is of a copper alloy and is, optionally, provided with a hollow cylindrical carbon insert in the passage 14.5 which extends over the length of the axially oriented passage 14.5.

Figure 12:
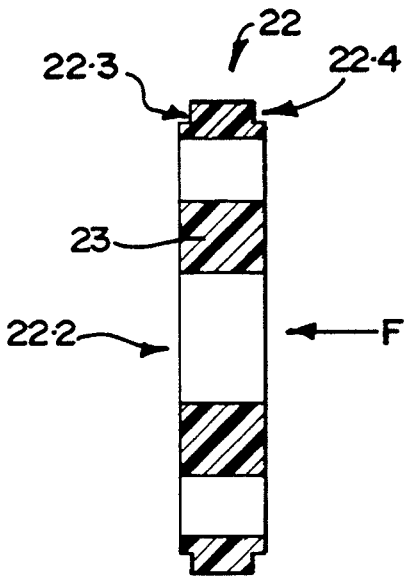
FIG. 12 is a sectional side view of the third housing component of the plasma torch of FIG. 1, this component being of an insulating material to constitute an insulator.
Figure 13:
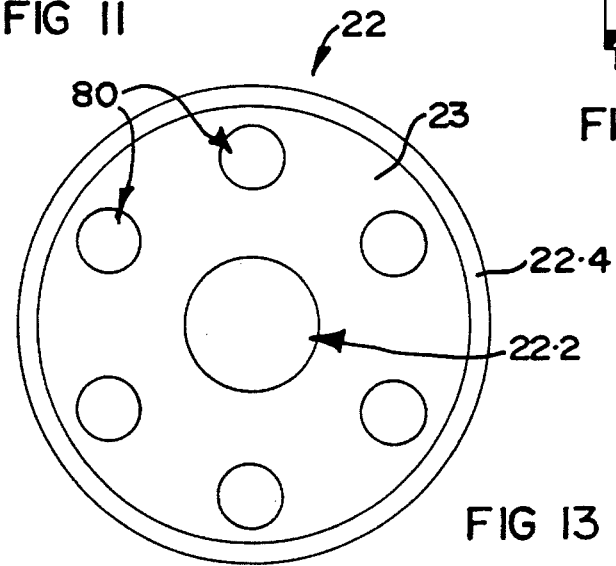
FIG. 13 is an end view of the housing component of FIG. 12, viewed in the direction of the arrow F in FIG. 12.

Referring to FIGS. 12 and 13, the insulator 22 consists of a disc shaped body 23 of polytetrafluoroethylene having a centrally located passage 22.2, extending through it. The body 23 abuts against the flange 42 of the component 20. The annular ridge 32.7 of the flange 42 is received in a complementary recess 22.3 on the outer edge on one side of the body 23. A corresponding recess 22.4 is located on the opposite side of the body 23.

Figure 14:
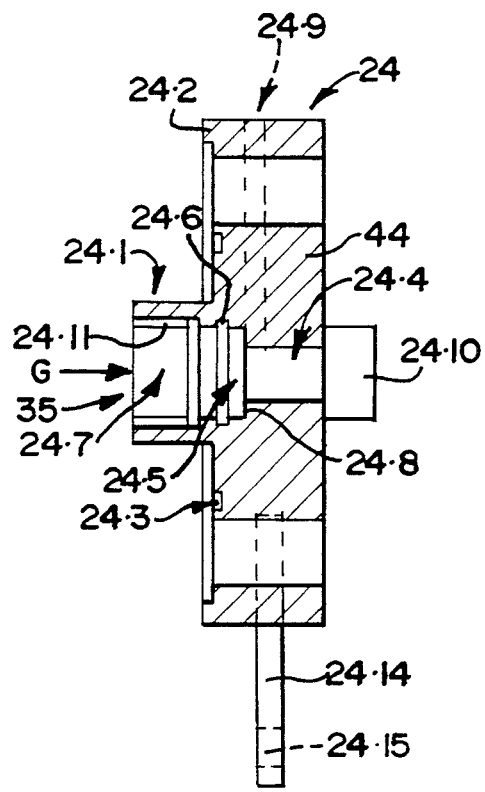
FIG. 14 is a sectional side view of the fourth housing component of the plasma torch of FIG. 1.
Figure 15:
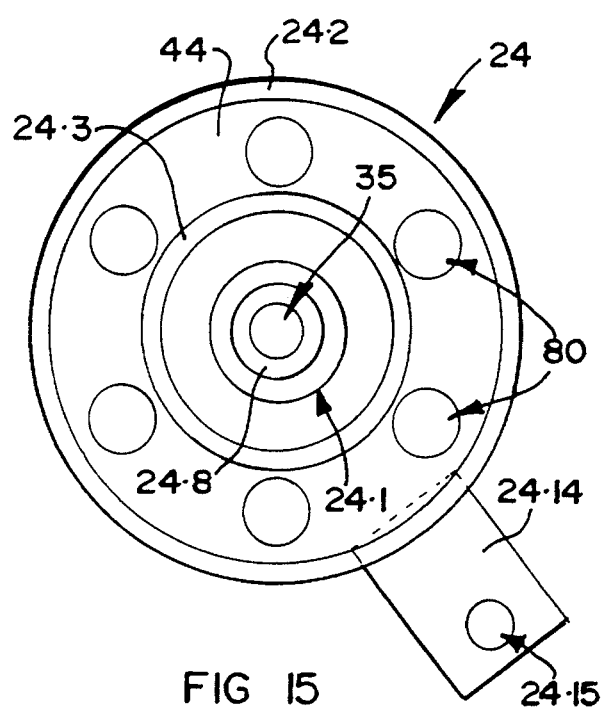
FIG. 15 is an end view of the housing component of FIG. 14, viewed in the direction of the arrow G in FIG. 14.

Referring to FIGS. 1, 14 and 15, the third housing component 24 also includes a hollow body 24.1 defining a passage 35 and an outwardly directed flange 44 at one end of the body 24.1. The component 24 is of stainless steel. The outer edge of the flange 44 has an annular ridge 24.2 which projects towards the body 24.1 and, in the plasma torch 10, is received in the complementary recess 22.4 of the insulator 22 (FIGS. 1 and 12). An annular groove 24.3 is provided in the flange 44 for receiving an O-ring. The inner profile of the passage 35 is stepped and includes, successively, a narrower portion 24.4, a wider portion 24.5, having an annular groove 24.6 for receiving an O-ring, and a still wider portion 24.7 which has a screw thread 24.11. In the plasma torch 10, the rear end portion 12.2 of the cathode 12 is received in the two passage portions 24.5, 24.7 and abuts against a shoulder 24.8 separating the narrower and wider portions 24.4, 24.5 (FIGS. 1 and 14). The screw thread 24.11 is engaged with a complementary screw threaded portion 12.9 of the cathode (FIG. 3) as is described below. A water outlet conduit 24.9 extends radially outwardly through the flange 44 from the passage 35. A Swagelok 24.10 (trade mark) is welded over the opening to the cylindrical passage 35 remote from the body 24.1. A stainless steel tube (not shown) passes through the Swagelok 24.10 and extends into the hollow interior of the cathode 12 as is described in further detail below.

A copper connector 24.14 with an opening 24.15 for attachment of an electrical cable (not shown) projects from the flange 44 for connecting the cable to the flange member 24.

Figure 3:
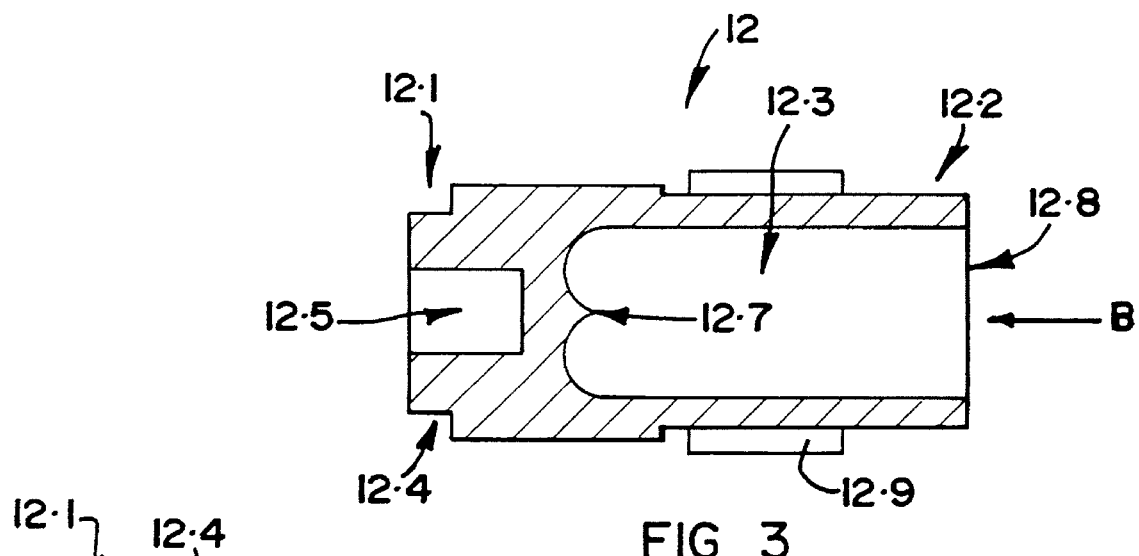
FIG. 3 is a sectional side view of the cathode of the plasma torch of FIG. 1.
Figure 4:
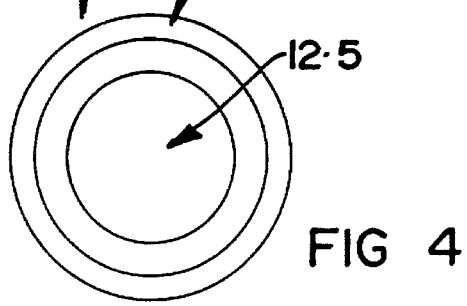
FIG. 4 is an end view of the cathode of FIG. 3, viewed in the direction of the arrow B in FIG. 3.
Figure 9:
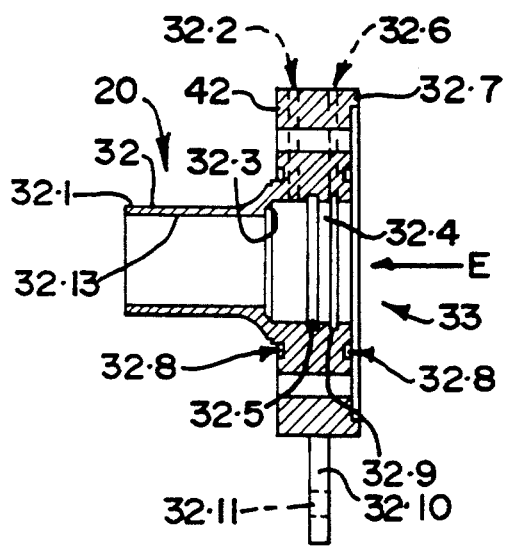
FIG. 9 is a sectional side view of the second housing component of the plasma torch of FIG. 1.
Figure 10:
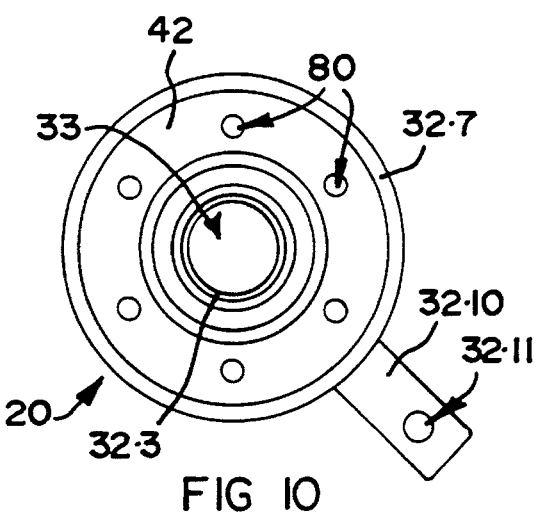
FIG. 10 is an end view of the housing component of FIG. 9, viewed in the direction of the arrow E in FIG. 9.
Figure 11:
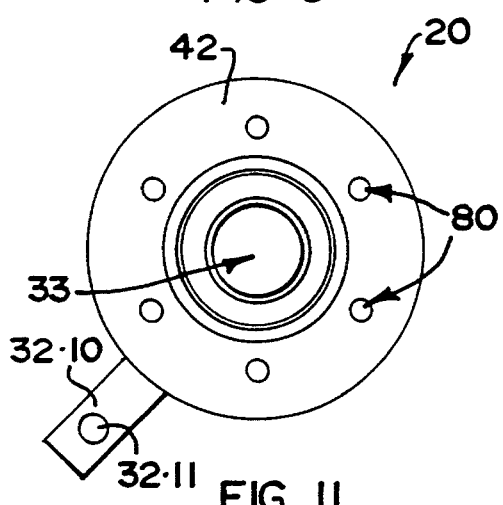
FIG. 11 is an end view of the housing component of FIG. 9 from the opposite end.

Referring now to FIG. 3, the cathode 12 is generally cylindrical in shape having, as mentioned above, a closed inner or operational end portion 12.1, an open outer end portion 12.2 with a rear opening 12.8, and a hollow interior 12.3. The closed end portion 12.1 has an annular shoulder 12.4. The cathode 12 is of a copper alloy. A screw threaded cylindrical opening 12.5 in which a graphite insert (not shown) is screw-threadedly received, extends into the closed end portion 12.1. In different embodiments of the invention, the insert is doped graphite or a high temperature metal alloy comprising tungsten, thoriated tungsten, other doped tungsten alloys, zirconium, hafnium, hafnium carbide, tantalum, tantalum carbide or any other suitable high temperature material. Such a cathode is generally referred to as a button type cathode. A centrally located externally screw threaded portion 12.9 is engaged with the screw threaded portion 24.11 of the housing component 24 as mentioned above. The end wall of the hollow interior 12.3 remote from the rear opening 12.8 has a curved profile 12.7. Referring to FIG. 1, in the plasma torch 10, the conduit 24.9 of the fourth housing component 24 opens into the passage 35 of the component 24 adjacent the rear opening 12.8 of the cathode 12. In use, cooling water is pumped into the hollow interior 12.3 of the cathode 12 through the stainless steel tube which passes through the Swagelok 24.10 to the end wall 12.7 and exits via the water outlet conduit 24.9 in the component 24, the curved profile 12.7 of the end wall improving flow distribution in the water flow. The cathode 12 is about 40 mm long and has a diameter, at its widest point, of about 20 mm.

Referring now to FIGS. 2, 8, 10, 11, 13 and 15, the flange 40 is provided with six screw-threaded holes 80 and the flanges 42, 44 and the insulator 22 are each provided with six complementary non-screw threaded holes 80 which are in register in the assembled state of the burner 10 depicted in FIG. 1. The holes 80 of the insulator 22 (FIG. 13) and the flange 44 (FIG. 15) have a larger diameter than those of the flanges 40, 42 (FIGS. 8 and 10) so that shoulders 84 are defined where the flange 42 abuts against the insulator 22 (FIG. 1).

Figures 22, 23:
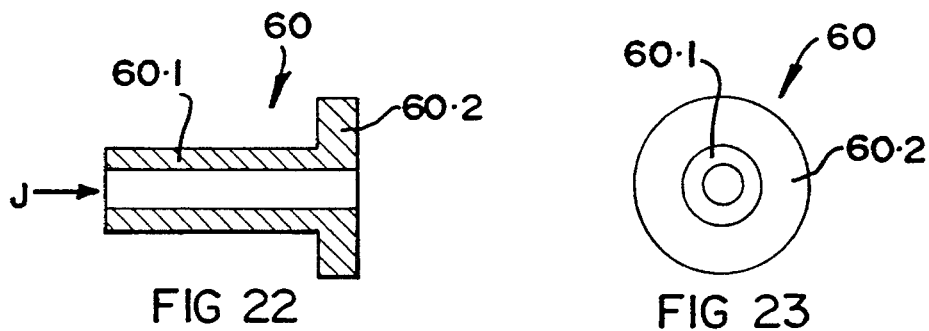
FIG. 22 is a sectional side view of an insulation washer.
FIG. 23 is an end view of the insulation washer of FIG. 23, viewed in the direction of the arrow J in FIG. 22.

Referring to FIGS. 1, 22 and 23, insulating washers 60 of Tufnol (trade mark) each having a hollow open-ended cylindrical body 60.1 and an outwardly directed annular head 60.2 projector inwardly into the holes 80 of the flange members 24, 22 with their heads abutting against the rear faces of the flanges 44 i.e., the faces remote from the insulator 22. The insulating washers are about 37 mm long.

Figures 18, 19:
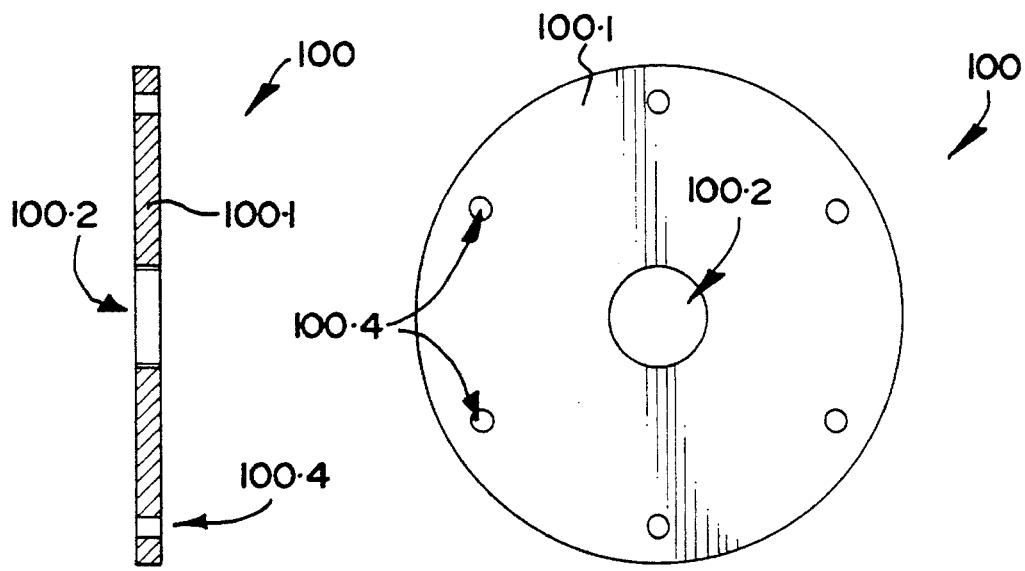
FIG. 18 is a sectional side view of a mounting flange for the plasma torch of FIG. 1.
FIG. 19 is an end view of the flange of FIG. 18.

Referring to FIGS. 18 and 19 the mounting flange 100 (not shown in FIG. 1) consists of a stainless steel disc 100.1 having a screw-threaded hole 100.2 in its centre. The screw-thread of the hole 100.2, in the assembled state of the torch 10, is engaged with the thread 30.5 of the component 18. The disc 100.1 is provided with six holes 100.4 speced symmetrically adjacent its outer edge for mounting the torch 10 on a reaction chamber (not shown).

Figures 20, 21:
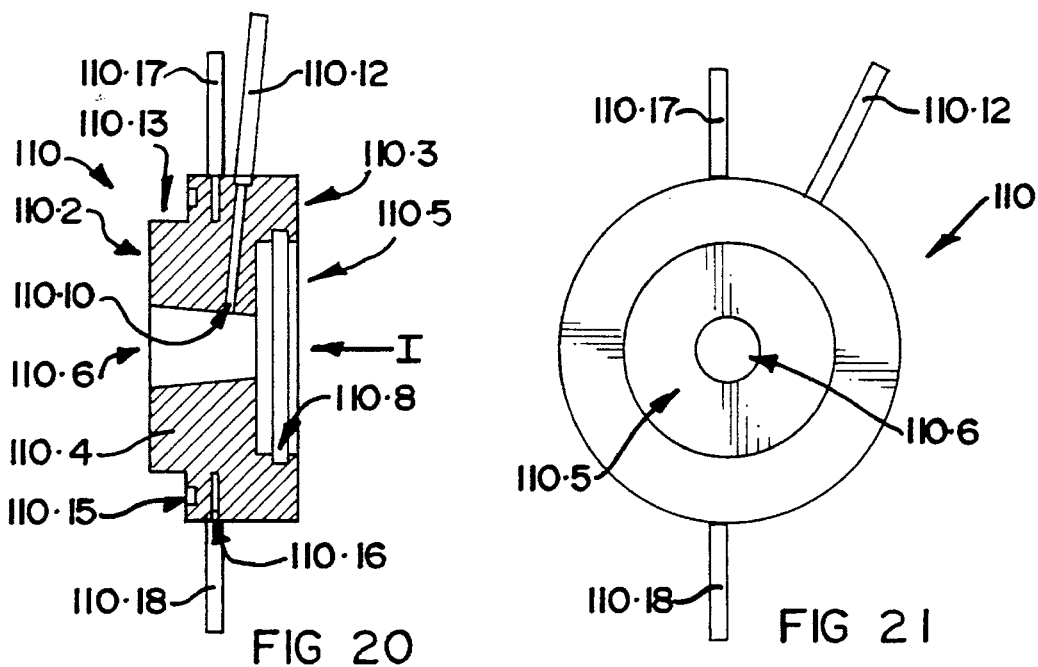
FIG. 20 is a sectional side view of a carbon feed component for the plasma torch of FIG. 1.
FIG. 21 is an end view of the feed flange of FIG. 20, viewed in the direction of the arrow I in FIG. 20.

Referring to FIGS. 20 and 21, a carbon feed flange 110 (not shown in FIG. 1) having a leading side 110.2 and a trailing side 110.3 consists of a hollow cylindrical body 110.4 with a wider opening 110.5 on the trailing side 110.3 and a narrower inwardly tapering opening 110.6 on its leading side 110.2. The wider opening 110.4 is provided with a groove 110.8 for receiving an O-ring and is dimensioned to fit over the end of the housing component 18 in the assembled torch 10. A carbon feed conduit 110.10 extends through the body 110.2 to the tapered opening 110.6 and is provided with an extension feed tube 110.12. The leading side 110.2 is provided around its periphery with an annular shoulder 110.13. The shoulder has an annular groove 110.15 for receiving an O-ring and the body 110.2 has a further circumferential passage 110.16 between the extension tube 110.12 and the shoulder 110.13 which is provided with a water inlet conduit 110.17 and a water outlet conduit 110.18 for the passage of cooling water to cool the carbon feed flange 110.

Bolts 81 serve to secure the housing components 18, 20, 22, 24 together.

In the plasma torch 10, the anode 14 and the cathode 12 are separated from one another by a small gap 97 (FIG. 1).

Figure 16:
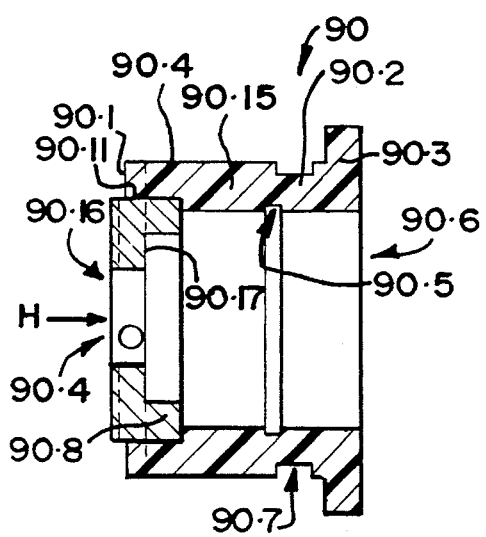
FIG. 16 is a sectional side view of the vortex generator of the plasma torch of FIG. 1, taken along line XVI—XVI in FIG. 17.
Figure 17:
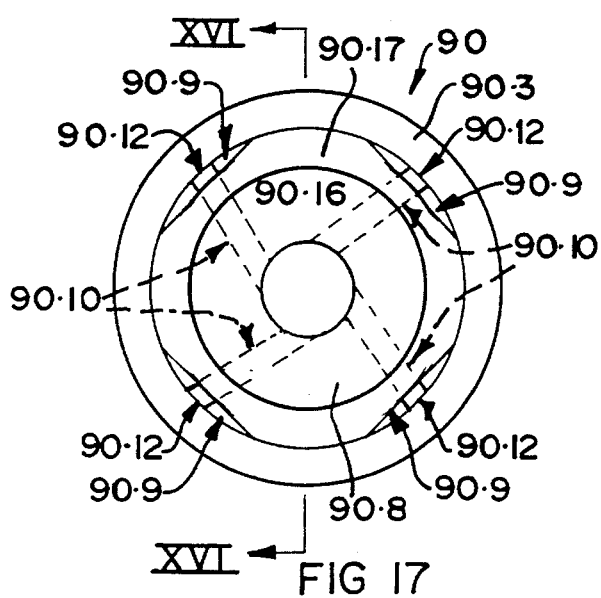
FIG. 17 is an end view of the vortex generator of FIG. 16, viewed in the direction of the arrow H in FIG. 16.

Referring now to FIGS. 1, 16 and 17, a vortex generator 90 separates the closed-end 12.1 of the cathode 12 from the cup-shaped portion 14.1 of the anode 14 (FIG. 1). The vortex generator 90 has a stepped inner cross-sectional profile complementary to the profile of the closed end 12.1 of the cathode 12 as can be seen, in particular, in FIG. 16.

The vortex generator 90 has a generally cylindrical body 90.15 which is hollow and open-ended and has a rear opening 90.6 and a front opening 90.4, with a cylindrical passage extending through it. It is about 20 mm long and has a diameter of about 26 mm. An annular pyrophyllite insert 90.8 with a centrally located opening 90.16 is located in the opening 90.7 and projects slightly from the cylindrical body 90.15 so that a shoulder 90.1 is defined around the periphery of the opening 90.7. The insert 90.8 and the cylindrical body 90.15 together have an inner profile complementary to that of the inner end portion 12.1 of the cathode 12 (FIG. 1). The pyrophyllite insert has an inner recessed face 90.17.

The body 90.15 is of polytetrafluoroethylene. In the plasma torch 10, the vortex generator 90 projects into the cylindrical opening 14.4 of the anode 14 so that the shoulder 90.1 abuts against the shoulder 14.10 of the anode 14. The vortex generator 90 has a rear flange portion 90.3 and an outer generally cylindrical face 90.4 which abuts against the inside of the opening 14.4 of the anode 14 (FIG. 1). The flange 90.3 acts as an insulator and fits into an annular space 59 defined between the inner end portion 14.1 of the anode, the flange 42 and the insulator 22 (FIG. 1 ). An annular groove 90.5 for receiving an O-ring is provided on the inner surface of the cylindrical passage and an annular groove 90.7 is provided on the outer face 90.4 next to the perspex ring 90.3. Four longitudinal grooves 90.9 in the form of a cut-away portion of the outer face 90.4 (FIG. 17) extend from the annular groove 90.7 to the shoulder 90.1. The projecting portion of the pyrophyllite insert is provided with four tangentially directed passages 90.12 extending inwardly from the grooves 90.9 to four tangentially directed grooves 90.10 on the recessed inner face 90.17 of the insert 90.8 and leading to the opening 90.16 in the insert 90.8 (FIG. 17) to create a tangential gas flow.

In the plasma torch 10, the gas conduit groove 32.9 of the housing component 20 is in register with the holes 14.3 in the anode 14 and the groove 90.7 of the vortex generator 90 and allows gas to be pumped via the conduit 32.9, the groove 32.10, the holes 14.3, the grooves 90.7, 90.9, the passages 90.12, and the grooves 90.10 into the gap 97 between the anode 14 and the cathode 12 where the tangentially directed gas streams cause a vortex in the gap 97.

The inside diameter and the length of the anode 14 play a critical role in the stabilisation of the arc and in the voltage characteristics of the plasma torch 10. In different embodiments of the invention different exit diameters are used so that the pressure inside the torch can be regulated. In use, the cooling of the anode 14 and particularly of the other sealing areas is of critical importance and water at pressures above 4 bar and flows in excess of 100 l/h are used to cool the anode 14 and the cathode 12.

In use, an arc is generated in the plasma torch 10 between the anode 14 and the cathode 12 and an input gas stream containing a fluorocarbon compound is fed via the gas inlet conduit 32.6 of the member 42 and the vortex generator 98 into the arc, where a plasma containing reactive species produced from the fluorocarbon compound is formed. The plasma leaves the plasma torch 10 through the passage 14.5 in the anode 14 (FIG. 5). The reactions which take place in the plasma, and after the plasma has been cooled, are described with reference to FIGS. 26–35 below.

Figure 26:
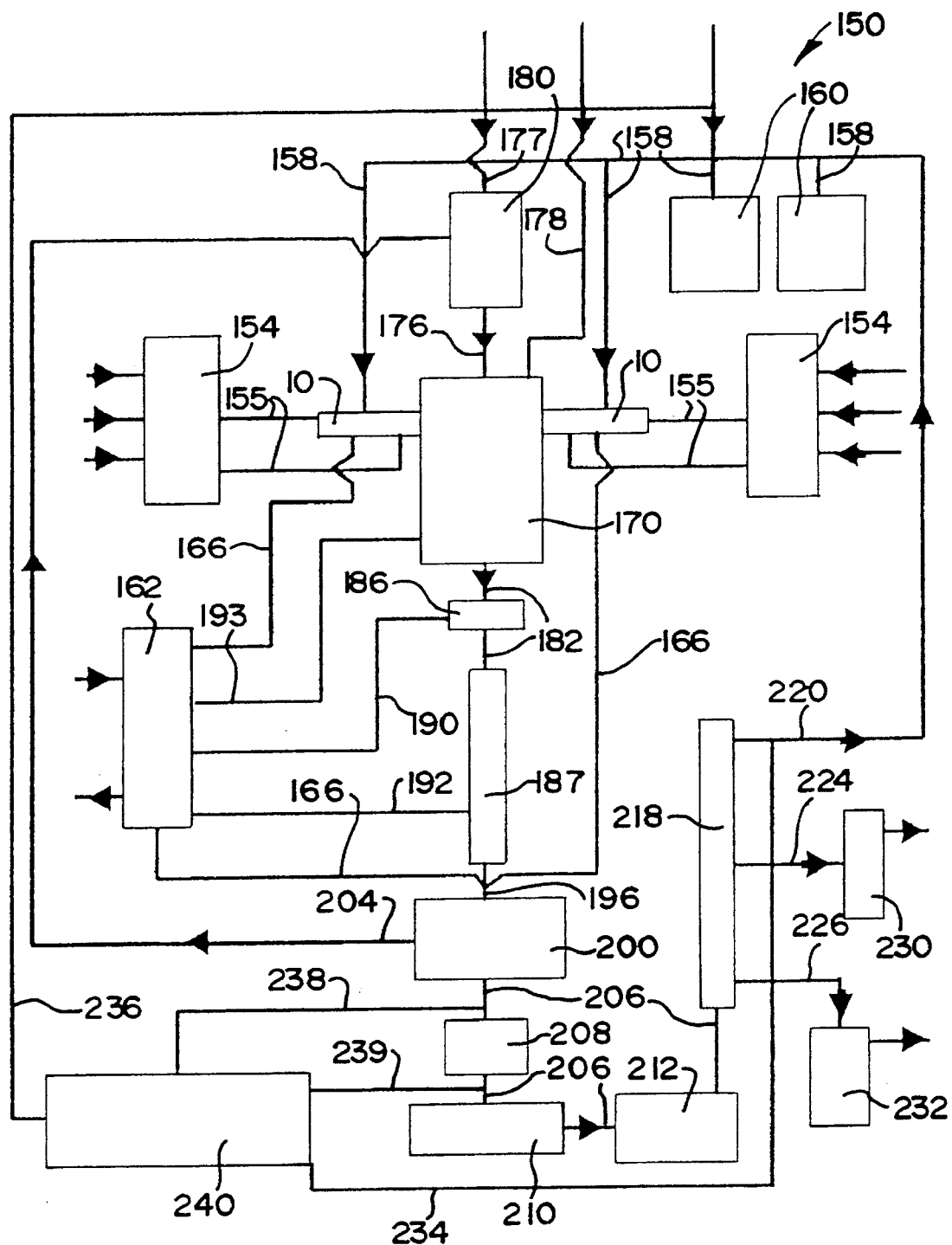
FIG. 26 is a schematic flow diagram depicting an installation for carrying out a process according to the invention for producing a desired fluorocarbon compound.
Figure 27:
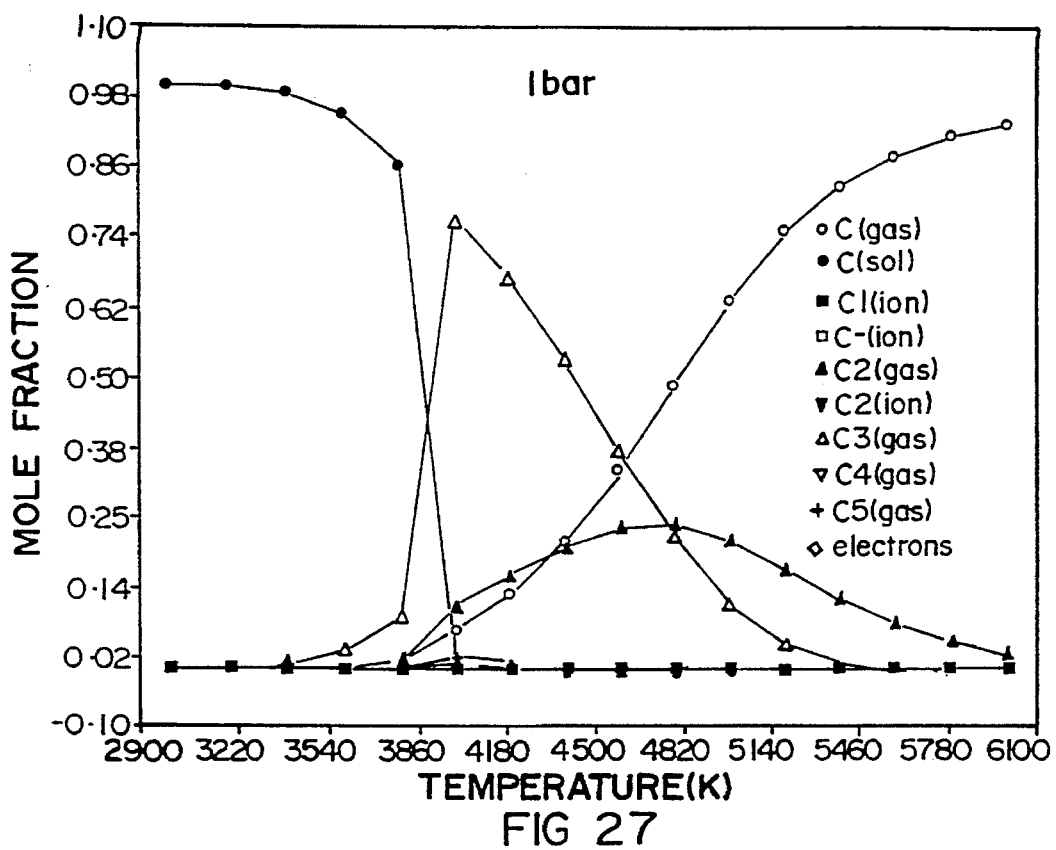
FIGS. 27 to 30 depict a set of four graphs showing thermodynamic equilibrium data for carbon at different pressures.
Figure 28:
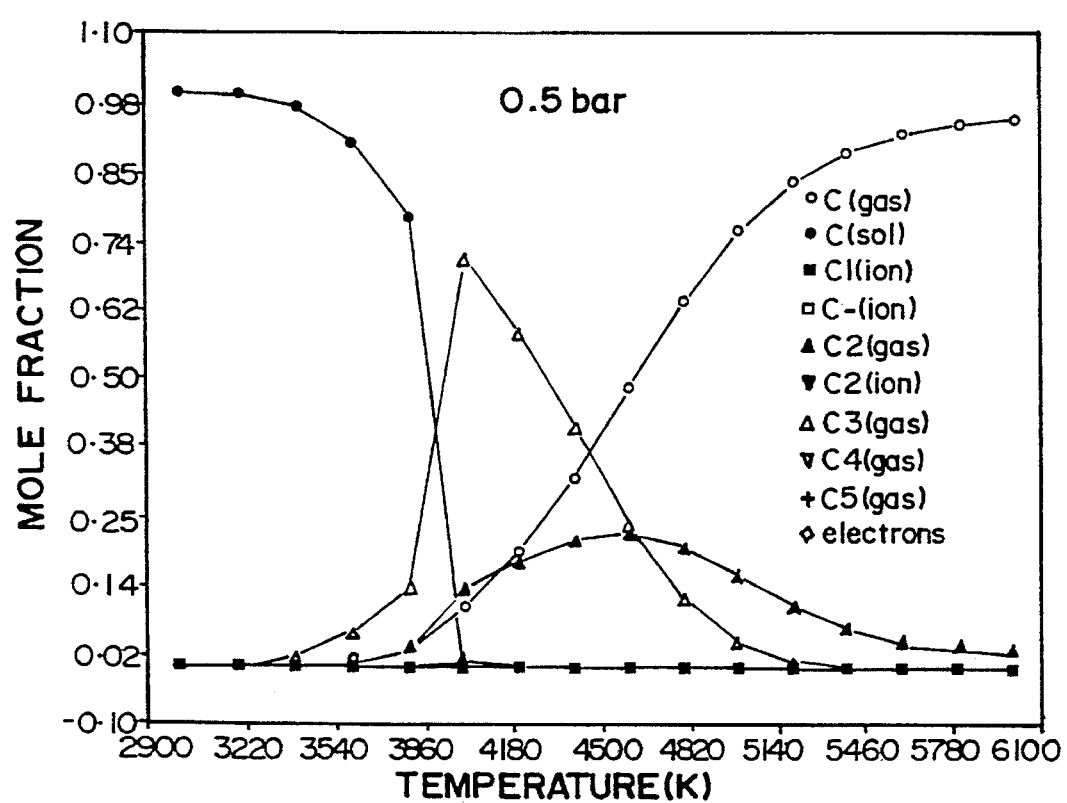
Figure 29:
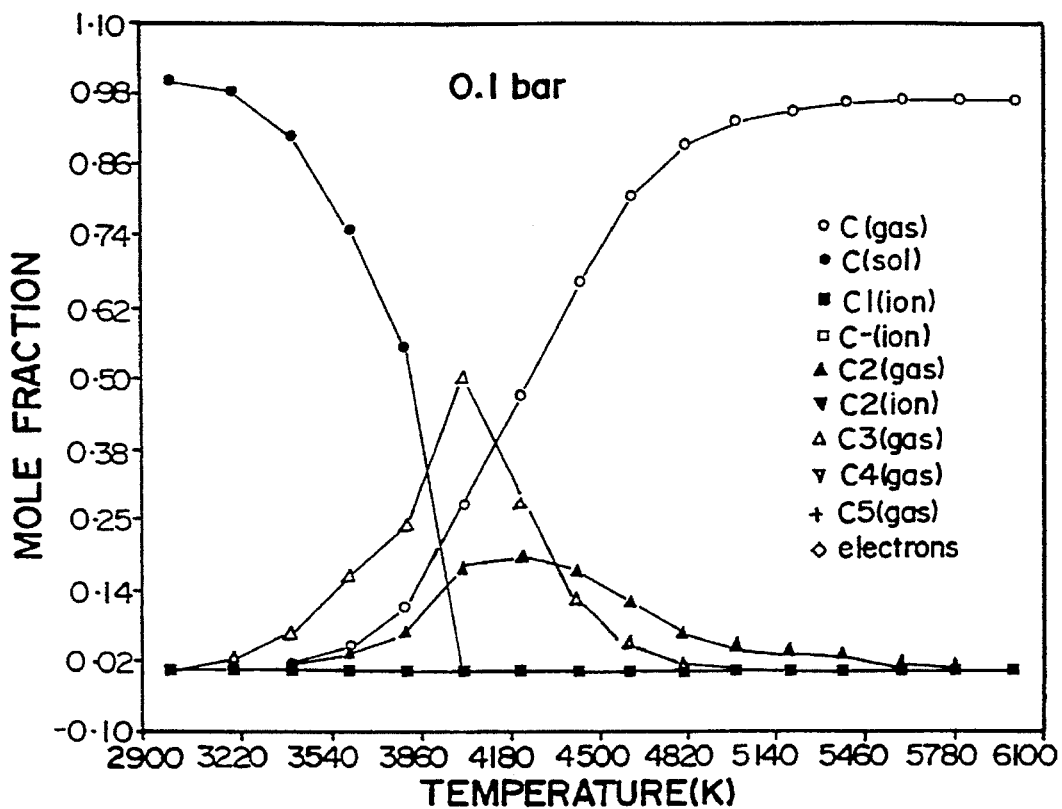
Figure 30:
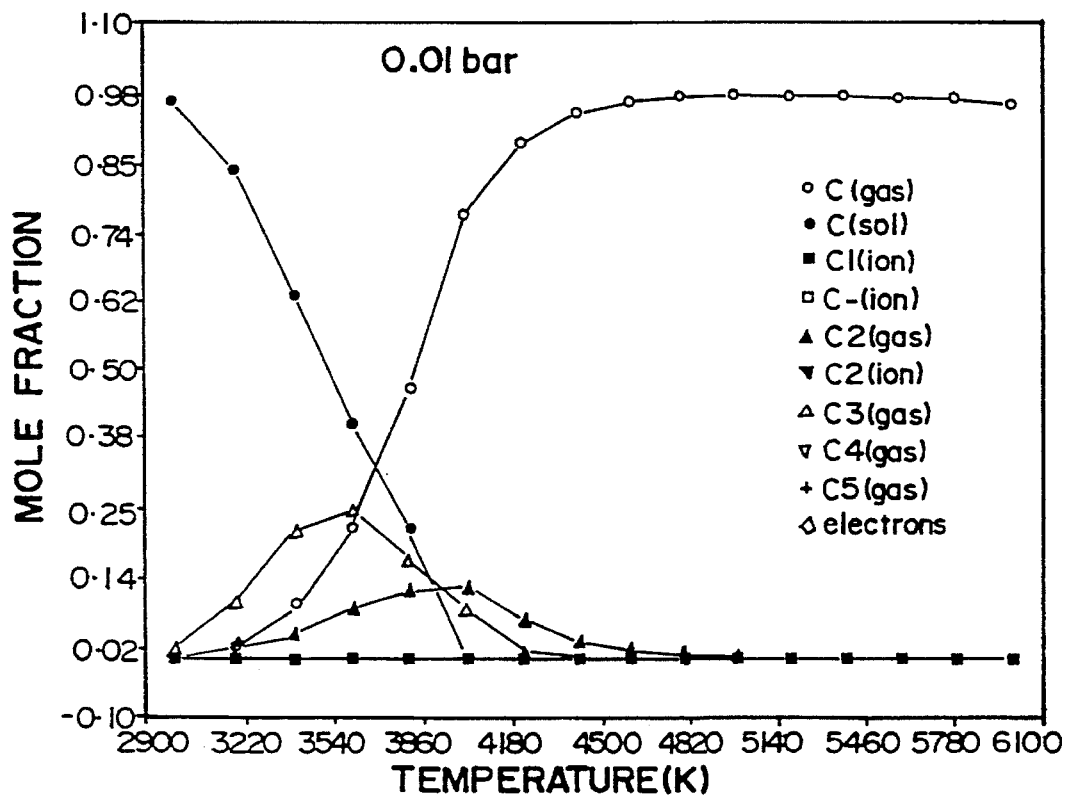

Referring to FIG. 26 of the drawings, reference numeral 150 depicts a schematic flow diagram of an installation in accordance with the invention for preparing fluorocarbon compounds. The installation 150 includes a pair of plasma torches 10 as described above, which are connected to power sources 154 by electrical connectors 155. Flow lines 158 extend from two fluorocarbon compound storage vessels 160 to the plasma torches 10. Water for cooling the anodes 14 and the cathodes 12 of the plasma torches 10 is fed from a supply tank 162 via flow lines 166. Each line 166 is a double line allowing flow to and from the torches 10.

The plasma torches 10 are mounted to feed reactive thermal plasma into a mixing chamber 170. Feed flow lines 176, 178 respectively are arranged to feed particulate carbon and fluorine into the mixing chamber 170. The feed line 176 extends from a carbon hopper 180. A feed line 177 leads into the hopper 180. A flow line 182 connects the mixing chamber 170 via a quench chamber 186, to a production reactor 187. Feed lines 190, 192, 193 feed cooling water from the water tank 162 to the quench chamber 186, the production reactor 187 and the mixing chamber 170. The lines 190, 192, 193 are double lines as described above. A flow line 196 extends from the production reactor 187 to a phase separator 200 from where a flow line 204 leads back to the carbon hopper 180 for returning carbon separated in the phase separator 200 to the mixing chamber 170. From the phase separator 200 a flow line 206 leads via a trap 208, a vacuum pump 210 and a compressor 212 to a phase separation and purification installation 218.

From the installation 218 flow lines 220, 224, 226 respectively lead to the fluorocarbon storage vessels 160, a fluorocarbon storage vessel 230 and a tetrafluoroethylene storage vessel 232.

An analytical facility 240 is shown schematically connected by a line 234 to the output flow lines 220, 224, 226 from the gas separation and purification installation 218; by a line 236 to the feed flow lines 174, 177, 178, 158; by a line 238 to the line 206 between the phase separator and the trap 208; and by a line 239 to the line 206 between the trap 208 and the vacuum pump 210 The analytical facility is provided with analytical apparatus for gas chromatographic, infrared and ultraviolet analyses.

In use, each power source 154 provides direct current in excess of 50 A at a voltage in excess of 100 V. Ripple as large as 10% can be accommodated on a small scale (<100 kW) but on a larger scale harmonics which can be generated and sent back to the input supply line would preferably be filtered out. Power output is regulated by adjusting the current, and the voltage used is determined by the type of gas, the pressure and the gas flow through the arc. At a power output of about 50 kW the voltage is between about 50 and 300 V. Each power source 154 is short circuit protected.

A gaseous fluorocarbon such as $CF_4$ is introduced into the arc of the plasma burners 10 from one of the storage tanks 160 via the line 158. The arc and the rate of addition are regulated so as to maintain a specific enthalpy between 1 and 10 kWh/kg in the plasma. The gas is introduced tangentially via the vortex generator 90, as described above, the geometry of the vortex generator causing the gas to spin at a high velocity between the electrodes. A starting gas, such as argon, is not required but may be introduced before or with the fluorocarbon. The magnetic coil 37 is optionally used to generate a magnetic field which causes rotation of the arc in the direction of rotation of the vortex.

The plasma generated in the arc, which contains a mixture of reactive species including reactive precursors such as $CF_2$, $C_2F_2$, $CF_3$, CF, C and F (referred to above), then passes into the mixing chamber 170. Particulate carbon is introduced into the tail flame of the plasma torches 110, which projects into the mixing chamber 170, via the feed line 176 from the hopper 180, the temperature of the plasma being reduced by heat transfer to the carbon and to the walls of the mixing chamber. The optimum yield of the precursors $CF_2$ and $C_2F_2$ for the production of the desired fluorocarbon products, is obtained in the temperature range 2300 K.–2700

Figure 31:
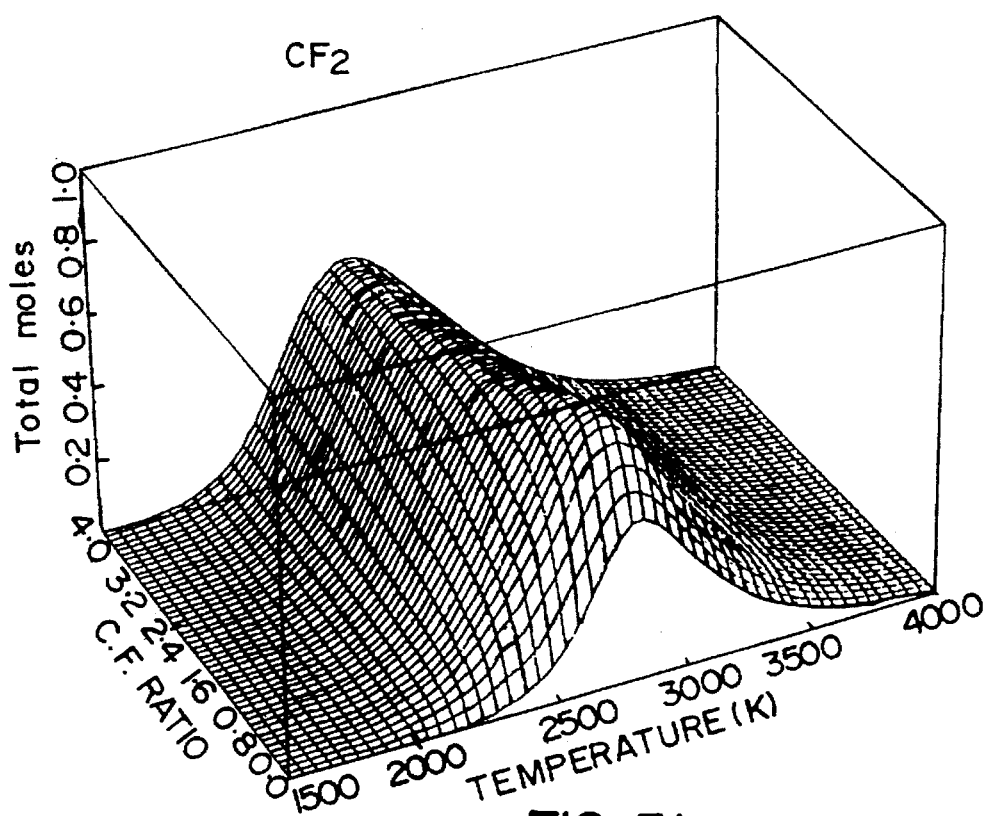
FIGS. 31 and 32 show a set of two three-dimensional graphs depicting the influence of the C:F ratio and the temperature on precursor yield at a pressure of 0.1 atmosphere.
Figure 32:
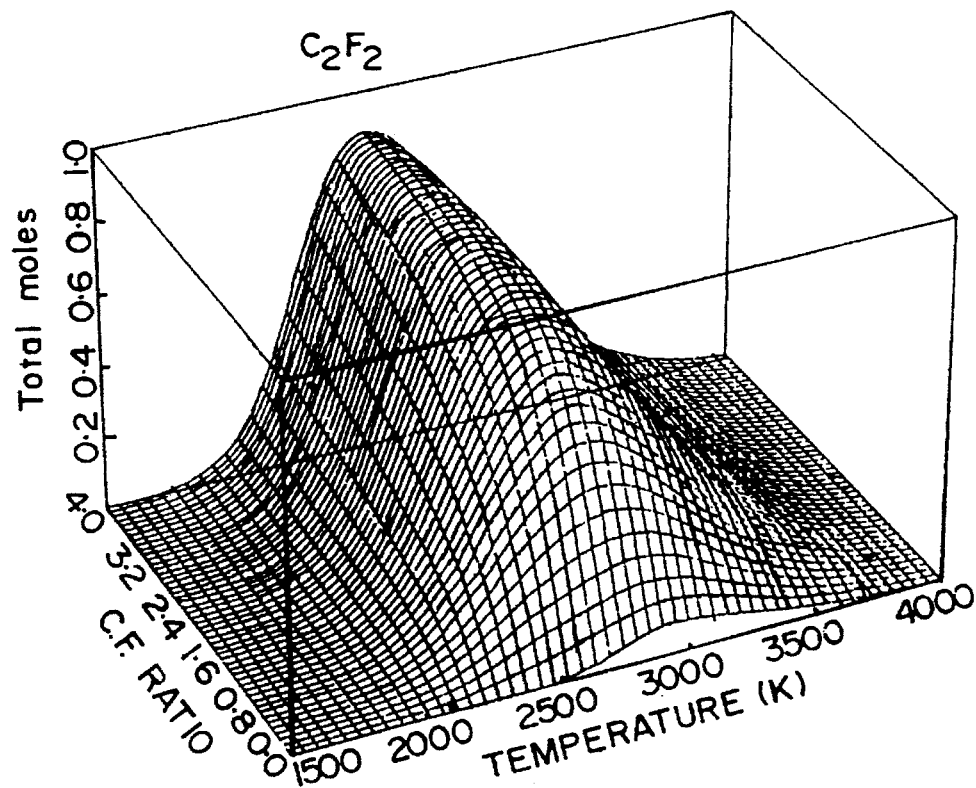
Figure 33:
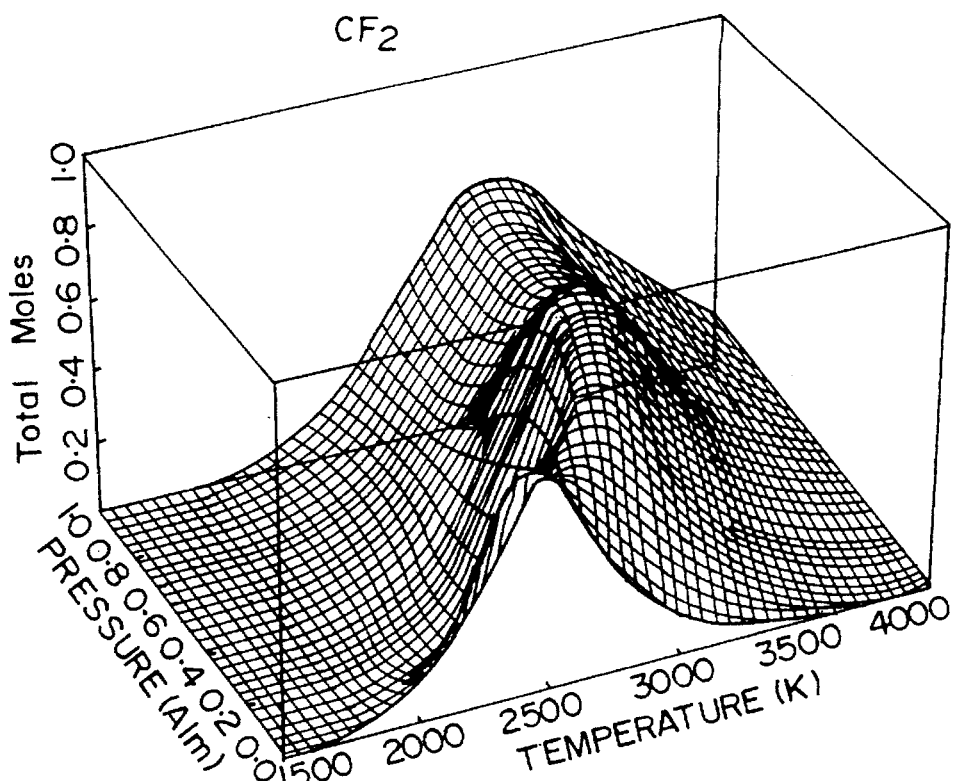
FIGS. 33 and 34 show a set of two three-dimensional graphs depicting the influence of pressure and temperature on precursor yield at a C:F ratio of 1.0.
Figure 34:
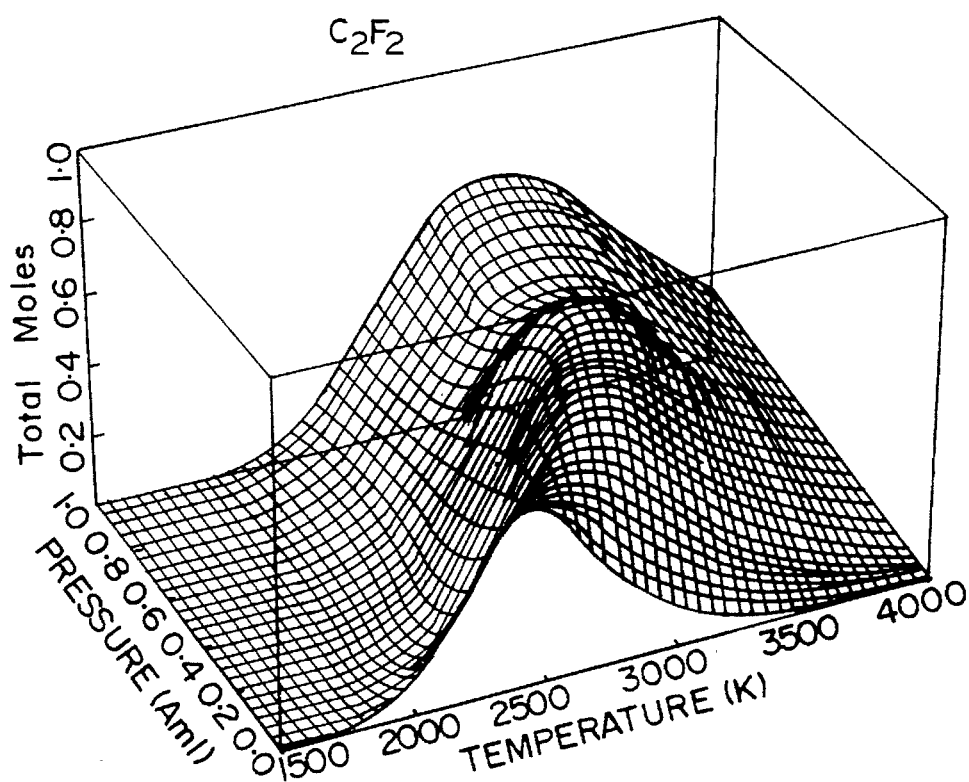

K. and the pressure range 0.1–1 bar, and preferably about 0.1 bar, as can be seen in FIGS. 33 and 34. The kinetics, heat transfer properties and reaction time of the plasma and the carbon particles influence the precursor concentrations. By maintaining the C:F ratio between 0.4 and 2.0 as can be seen in FIGS. 31 and 32, and by maintaining the enthalpy of the system between about 1–10 kWh/kg of feed gas, the precursor concentrations can be optimised.

The precursors are cooled in the quench chamber 186 during and after which the precursors react both in the quench chamber 186 and in the production reactor 187 to form a product mixture comprising $C_2F_4$ (TFE), $C_2F_6$, $C_3F_8$, $C_3F_6$, and $CF_4$. By controlling this step of the process, as described above, the yields of selected compounds can be optimised. In particular, cooling the precursors to below 300 K. in less than 0.05 seconds results in an optimised yield of TFE.

Carbon particles are removed from the product mixture by passing the mixture through a ceramic filter in the phase separator 200 and the removed carbon is recycled to the hopper 180 via the line 204. The hopper 180 is designed to feed carbon into the mixing chamber 170 at a rate which varies between 0.1 g/min and more as may be required.

The filtered product mixture is then passed through the chemical trap 208 containing carbon at 700 K. to remove $F_2$, the vacuum pump 210 and the compressor 212. The vacuum pump 210 is designed to evacuate the total system to less than 0.01 bar and to pump large volumes of gas (above 1 l/min). Both the pump 210 and the compressor 212 are also designed to withstand impurities such as HF and $F_2$.

After compression in the compressor 212, the compressed product mixture is separated by distillation in the phase separation and purification installation 218 and stored in the storage vessels 230, 232. Unwanted fluorocarbons are recycled to the storage vessels 160.

Product gases are analysed on a continuous basis. All product gases pass through an infrared cell and the intensity of the IR bands of specific products are monitored. Samples are also removed for gas chromatographic analysis using a Porapak Q packed stainless steel column. UV-visible spectrophotometry is used to detect unreacted fluorine. Similar methods are used to analyse the end products.

In another embodiment of the invention particulate waste PTFE is fed into the mixing chamber 170 from the hopper 180.

Figure 24:
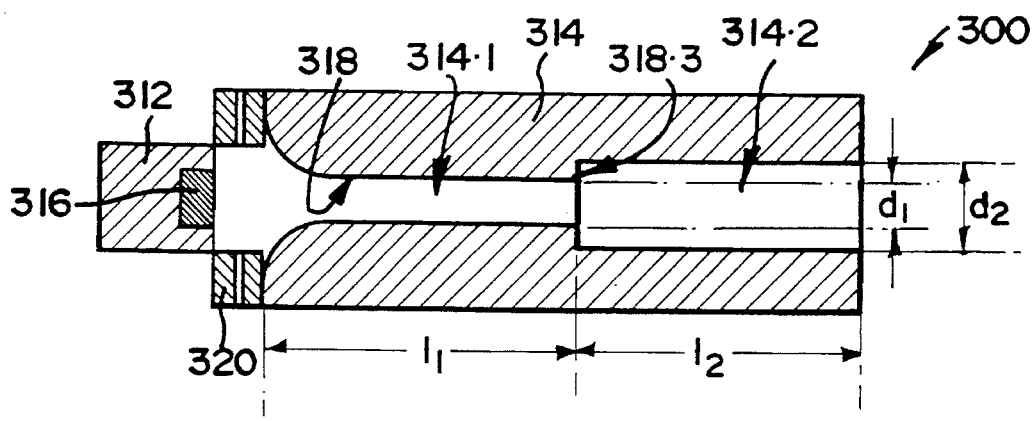
FIGS. 24 and 25 are sectional side views of alternative anode and cathode configurations to be used in a plasma torch in carrying out a process of the invention.
Figure 25:
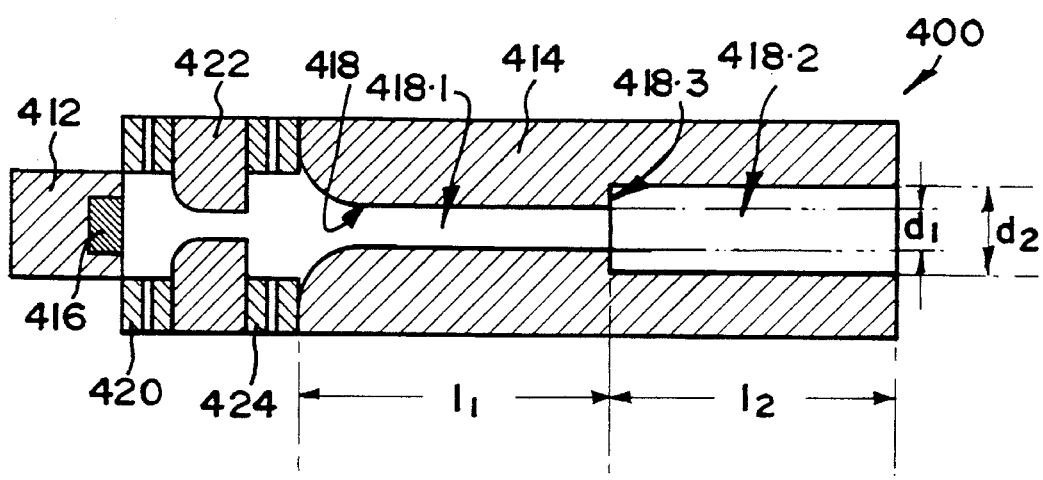

Referring now to FIGS. 24 and 25, two alternative electrode configurations are illustrated schematically. The configuration 300 depicted in FIG. 24 has a cathode 312 and anode 314 both of which may be of copper or a copper alloy. The cathode has an insert 316 of graphite or doped graphite. The anode 314 has an internal passage 318 of stepped configuration having a narrow portion 314.1 with diameter $d_1$ and length $l_1$ and a wider portion 318.2 with diameter $d_2$ and length $l_2$. The portions 314.1, 314.2 are separated by a stepped shoulder 318.3. A vortex generator or spinner is schematically shown as 320.

The configuration 400 of FIG. 25 has a cathode 412 and anode 414 of copper or copper alloy similar to those of FIG. 24, the cathode 412 having an insert 416 of graphite or optionally doped graphite. The anode 414 again has an internal passage 418 of stepped configuration, with a stepped shoulder 418.3 separating a narrow portion 418.1 with diameter $d_1$, and length $l_1$, and a wider portion 418.2 with diameter $d_2$ and length $l_2$.

In the case of FIG. 25, an insert is provided between two vortex generators or spinners 420, 424.

The invention and the manner in which it may be carried out in practice will now be described further by way of the following examples.

EXAMPLES 1–6

General Procedure

In Examples 1–6, the following general procedure was followed. A single plasma torch unit was used, with a water cooled tubular copper alloy anode and a water cooled button type copper alloy cathode with a graphite insert (generally of the type as shown in FIGS. 24 and 25). The inner diameter of the anode in the region adjacent the cathode was 4 mm while the diameter of the remainder of the anode was 8 mm.

This plasma unit was connected to a carbon feeder with 3 equally spaced 1 $mm^2$ inlets through which carbon was fed from the hopper. Carbon tetrafluoride ($CF_4$) was used as carrier gas to feed carbon perpendicularly into the plasma tail flame directly below the anode. The reactor chamber directly underneath the carbon feeder was water cooled, and had a graphite lining and an inside diameter of 50 mm.

A water cooled heat exchanger (quench probe) was provided inside the reactor chamber 60 mm below the anode. The heat exchanger quenched the precursor mixture from enthalpies above 2 kWh/kg to enthalpies in the vicinity of 0.001 kWh/kg. The mass flux through the heat exchanger during the exemplary procedures was approximately 0.4 $g/(s \cdot cm^2)$.

Afterwards the gaseous product was passed through another heat exchanger. Excess carbon particles were removed with polytetrafluoroethylene or stainless steel porous filters. The clean gas was monitored continuously for the presence of tetrafluoroethylene by means of infrared spectrophotometry at 1330 $cm^{-1}$. Samples were taken for gas chromatographic analyses during the procedures.

A carbon tetrafluoride plasma gas flow rate of 2.36 kg/h was used. The power input to the plasma ranged from 13 kW (100 A, 130 V) to 25 kW (249 A, 106 V). The enthalpy of the plasma gas ranged accordingly from 3.02 kWh/kg to 6.7 kWh/kg. The efficiency of the plasma torch varied between 50 and 75%, while the efficiency of the total system varied between 39% and 62%.

EXAMPLE 1

Production of Tetrafluoroethylene (TFE) from Carbon Tetrafluoride ($CF_4$)

The general procedure was followed using $CF_4$ as plasma gas. A feed rate of 2.36 kg/h $CF_4$ into the plasma torch was used. The plasma gas was spun in through four 1.57 $mm^2$ inlets just below the cathode. Carbon of 18 μm particle size was injected into the plasma tail flame through three 1 $mm^2$ gaps. A $CF_4$ carrier gas feed of 0.72 kg/h was used. A carbon feed rate of 4 g/min average was maintained. The power supplied to the plasma source was 21.7 kW. The results are given in Table 1.

TABLE 1

| $CF_4$ plasma with carbon feed into the flame to produce $C_2F_4$ | |
|---|---|
| PRODUCT | 21 kW |
| $CF_4$ | 65% |
| $C_2F_4$ | 26.5% |
| $C_2F_6$ | 7.2% |

The pressure inside the plasma reactor was maintained at 0.1 bar (abs). A C:F ratio of 0.4 was maintained. The enthalpy of the $CF_4$ plasma flame was calculated as 6 kWh/kg. The plasma mixture was quenched from an enthalpy of 4.2 kWh/kg. The mass flux through the quench probe was calculated as 0.46 $g/(s \cdot cm^2)$. The 26.5 mole % yield of $C_2F_4$ corresponds to a specific enthalpy of 25 kWh/kg TFE and a TFE production rate of 0.89 kg/h $C_2F_4$. The procedure was stopped voluntarily after 21 minutes.

EXAMPLE 2

Production of Tetrafluoroethylene (TFE) from Carbon Tetrafluoride $CF_4$

Example 1 was repeated with a $CF_4$ carrier gas flow which varied from 0.64 kg/h to 0.68 kg/h. Carbon of a 3 µm particle size was fed at a 25 g/min feed rate into a plasma tail flame. The power input to the plasma ranged from 19 kW to 21 kW. The results are given in Table 2A and 2B.

TABLE 2A $CF_4$ plasma with carbon feed into the flame to produce $C_2F_4$

| PRODUCT | 19.7 kW | 20 kW | 21 kW |
| --- | --- | --- | --- |
| $CF_4$ | 77.2% | 70.2% | 67.8% |
| $C_2F_4$ | 12.6% | 21.2% | 24.4% |
| $C_2F_6$ | 10.2% | 8.5% | 7.9% |
| $CF_4$ carrier gas | 0.64 kg/h | 0.7 kg/h | 0.68 kg/h |

TABLE 2B $CF_4$ plasma with carbon feed into the flame to produce $C_2F_4$

| PRODUCT | 19.7 kW | 20 kW | 21 kW |
| --- | --- | --- | --- |
| Enthalpy in plasma tail flame | 5.9 kWh/kg | 5.8 kWh/kg | 6 kWh/kg |
| Quench from enthalpy | 3.57 kWh/kg | 3.65 kWh/kg | 4.28 kWh/kg |
| Energy required for 1 kg of TFE | 49.6 kWh | 29 kWh | 26.7 kWh |
| TFE production rate | 0.41 kg/h | 0.71 kg/h | 0.81 kg/h |

The reaction was run at 0.1 bar (abs). A C:F ratio of 1.2 was maintained. The procedure was voluntarily stopped after 15 minutes.

EXAMPLES 3–5

Production of Tetrafluoroethylene (TFE) from Hexafluoroethane $C_2F_6$

The general procedure was followed using a $C_2F_6$ plasma gas feed into the torch of 2.3 kg/h. The $C_2F_6$ was spun into the torch through four 1.77 mm$^2$ inlets just below the cathode. The experiment was conducted at energy inputs between 13 kW and 23 KW. The results are given in Table 3. More information is given in Table 4 and 5.

TABLE 3

$C_2F_6$ feed into the plasma source to produce $C_2F_4$

| PRODUCT | Example 3 13.3 kW | Example 4 19.8 kW | Example 5 23.4 kW |
| --- | --- | --- | --- |
| $CF_4$ | 66.8% | 58.4% | 55.9% |
| $C_2F_4$ | 26.5% | 32.4% | 36.1% |
| $C_2F_6$ | 6.7% | 7.8% | 8% |
| $C_3F_6$ | 0% | 1.4% | 0% |

TABLE 4

$C_2F_6$ feed into the plasma source to produce $C_2F_4$

| Power input (kW) | Enthalpy in plasma flame (kWh/kg) | Quench from enthalpy (kWh/kg) |
| --- | --- | --- |
| Example 3 (13.3 kW) | 2.96 | 2.77 |
| Example 4 (19.8 kW) | 5.16 | 4.51 |
| Example 5 (23.4 kW) | 6.41 | 5.61 |

TABLE 5

$C_2F_6$ feed into the plasma source to produce $C_2F_4$

| Mole % yield $C_2F_4$ | Specific enthalpy $C_2F_4$ | $C_2F_4$ production rate |
| --- | --- | --- |
| Example 3 (26.5%) | 20.8 kWh/kg TFE | 0.65 kg/h TFE |
| Example 4 (32.4%) | 25.6 kWh/kg TFE | 0.78 kg/h TFE |
| Example 5 (36.1%) | 27.4 kWh/kg TFE | 0.87 kg/h TFE |

The pressure in the plasma reactor was maintained at 0.1 bar (abs). The C:F ratio was 0.3. At a flame enthalpy of 6.41 kWh/kg a gas mixture temperature of 4000 K. was reached and the graphite lining started to evaporate. The mass flux through the quench probe was 0.46 g/(s·cm$^2$). The experiments were voluntarily stopped after 6 minutes.

EXAMPLE 6

Production of Tetrafluoroethylene (TFE) from Hexafluoroethane $C_2F_6$

The procedure of Examples 3–5 was repeated with the difference that carbon was fed into the plasma tail flame. Carbon of 42 µm mean particle size (36–53 µm) was injected into the $C_2F_6$ plasma tail flame through three 1 mm$_2$ gaps at a feed rate of 46.9 g/min. $C_2F_6$ was also used as carrier gas at a feed rate of 1.8 kg/h. The experiment was done with a 19 kW (161 A, 119 V) power supply to the plasma source. The results are given in Table 6.

TABLE 6

$C_2F_6$ plasma with carbon feed into the flame to produce $C_2F_4$

| PRODUCT | 19 kW |
| --- | --- |
| $CF_4$ | 63.5% |
| $C_2F_4$ | 27.9% |
| $C_2F_6$ | 7.4% |
| $C_3F_6$ | 1.2% |

The enthalpy in the $C_2F_6$ plasma flame was calculated as 5.61 kWh/kg. The plasma gas mixture was quenched at an enthalpy of 2.52 kW/kg. The mass flux through the quench probe was 0.6 g/(s·cm$^2$). A C:F ratio of 1.6 was fed. The 27.9 mole % TFE yield corresponds to a specific enthalpy of 16 kWh/kg TFE and a production rate of 1.2 kg/h TFE. A reactor pressure of 0.1 bar (abs) was maintained. The experiment was voluntarily stopped after 4.5 minutes.

In developing the present invention, the Applicant has given particular attention to the design and development of a plasma torch capable of operating with corrosive plasma gases, such as fluorine and fluorocarbons, at the elevated temperatures (i.e., high enthalpy conditions) required for the various reactions to take place, and for commercially acceptable operation periods, i.e., at least several hours of continuous operation.

In experimental work with fluorine-containing plasmas using gases such as $CF_4$, and where use is made of graphite electrodes which are not intensely water cooled, it was found that the anode starts to evaporate if the current density becomes more than 50 $A/cm^2$.

Furthermore, in most plasma processes it is desirable for the amount of plasma gas to be minimised so as to minimise the cost of operation. Using only one plasma gas contributes to easy operation of the plasma and to the reduction of costs. Specifically in the production of TFE from fluorides and carbon, the use of additional plasma gases such as Ar or He will increase the scale of separation. The production of a plasma using only fluorine containing gases with conventional plasma torch designs is generally not successful because the gases decompose at high temperature to form very reactive and corrosive F species. These species react with most high temperature metals such as tungsten, hafnium and tantalum to form gases like $WF_6$, $HfF_x$ and $TaF_6$ and this causes very high electrode erosion rates. The Applicant has found that graphite does show chemical resistance to the F species when it is intensely cooled and kept at temperatures below 800 K.

The Applicant has found that graphite shows greater erosion rates when it is used as an anode. The reason is that the arc spot can heat the carbon to very high temperatures resulting in the formation of C positive ions.

Copper, nickel and copper/nickel alloys have also been found to show good resistance to chemical F corrosion at temperatures below 1300 K.

The invention envisages the provision of a plasma torch using only fluorine-containing gases as a plasmagas and offering high voltage, affordable electrodes, low electrode erosion rates, stable operation under various pressures, high enthalpy and relatively low gas flow rates.

The following Examples 7–10 illustrate the performance of different electrode configurations and materials in different operating conditions where a plasma torch was used with fluorocarbon plasma gases. The Examples are based on experimental work carried out by the Applicant.

EXAMPLE 7

A plasma torch consisting of a button cathode with an intensely water cooled graphite insert and a water cooled stepped copper anode, generally as shown in FIG. 24, was used for this experiment.
(a) Cathode: Button graphite water cooled
(b) Anode: Stepped copper water cooled $d_1/d_2=4/8$ mm and $l_1/l_2=33/15$ mm
(c) Plasma gas: $CF_4$
(d) Gas flow rate: 2.36 kg/h
(e) Volts: 127 V
(f) Current: 160 A
(g) Power: 20.3 kWh
(h) Erosion rate
  Cathode: 0.07 µg/C
  Anode: 0.6 µg/C
(i) Test time: 1 h
(j) Enthalpy: 5.54 kWh/kg $CF_4$
(k) Efficiency: 64%
(l) Inlet spin velocity: 26 m/s
(m) Pressure: 0.1 bar (abs)

This plasma torch was tested with $CF_4$ over a wide range of conditions with volts ranging from 100 to 150 V at currents between 100 and 250 amperes and enthalpies between 3 and 8 kWh/kg, and with erosion rates below 1.5 µg/C and efficiencies between 60 and 70%. The inlet spin velocities varied between 10 and 80 m/s.

EXAMPLE 8

A plasma torch using the design generally shown in FIG. 24 was used for this experiment.
(a) Cathode: Button graphite water cooled
(b) Anode: Stepped copper water cooled $d_1/d_2=4/8$ mm and $l_1/l_2=33/15$ mm
(c) Plasma gas: $C_2F_6$
(d) Gas flow rate: 2.30 kg/h
(e) Volts: 124 V
(f) Current: 160 A
(g) Power: 19.8 kWh
(h) Erosion rate
  Cathode: 0.18 µg/C
  Anode: 0.7 µg/C
(i) Test time: 45 minutes
(j) Enthalpy: 5.2 kWh/kg $C_2F_6$
(k) Efficiency: 60%
(l) Inlet spin velocity: 16 m/s
(m) Pressure: 0.1 bar (abs)

This plasma torch was tested over a wide range of conditions with volts ranging from 117 to 133 V at currents between 100 and 200 amperes and enthalpies between 3 and 6.5 kWh/kg, and with erosion rates below 1.5 µg/C and efficiencies between 55 and 70%.

EXAMPLE 9

A plasma torch with an insert between the anode and cathode was tested, of a design generally as shown in FIG. 25. Two gas flow rates were used, one between cathode and insert ($G_1$) and one between insert and anode ($G_2$).
(a) Cathode: Carbon button water cooled
(b) Insert material: Water cooled copper, 10 mm thick 5 mm internal diameter
(c) Anode material: Stepped water cooled copper $d_1/d_2=8/16$ mm and $l_1/l_2=60/55$ mm
(d) Plasma gas: $CF_4$
(e) Gas flow rate
  $G_1$: 5.4 kg/h
  $G_2$: 9.0 kg/h
(f) Volts: 230 V
(g) Current: 300 A
(h) Power: 69 kW
(i) Erosion rate
  Cathode: 0.05 µg/C
  Anode: 1 µg/C
(j) Test time: 20 minutes
(k) Enthalpy: 2.9 kWh/kg
(l) Efficiency: 60%
(m) Inlet spin velocity 1: 60 m/s
(n) Inlet spin velocity 2: 100 m/s
(o) Pressure: 1.0 bar (abs)

This plasma torch was tested over a wide range of conditions with volts ranging from 180 to 280 V at currents between 150 and 400 amperes, enthalpies between 1.5 and 4 kWh/kg, and with erosion rates below 1.5 µg/C and efficiencies between 50 and 80%.

EXAMPLE 10

A plasma torch with the design generally as shown in FIG. 25, was used to do this experiment at 1 bar (abs) with $CF_4$.

(a) Cathode: Carbon button water cooled
(b) Insert material: Water cooled copper, 10 mm thick 5 mm internal diameter
(c) Anode: Stepped water cooled copper $d_1/d_2=8/16$ mm and $l_1/l_2=60/55$ mm
(d) Plasma gas: $CF_4$
(e) Gas flow rate
  $G_1$: 2.7 kg/h
  $G_2$: 7.4 kg/h
(f) Volts: 190 V
(g) Current: 300 A
(h) Power: 57 kWh
(i) Erosion rate
  Cathode: 0.1 μg/C
  Anode: 1 μg/C
(j) Test time: 20 minutes
(k) Enthalpy: 3.2 kWh/kg
(l) Efficiency: 50%
(m) Inlet spin velocity $G_1$: 30 m/s
(n) Inlet spin velocity $G_2$: 80 m/s
(o) Pressure: 1 bar (abs)

This plasma torch was tested over a wide range of conditions with volts ranging from 180 to 280 volts at currents between 150 and 400 amperes, enthalpies between 1.5 and 4 kWh/kg and erosion rates below 1.5 μg/C and efficiencies between 50 and 80%.

The Applicant has found that the method and installation of the invention can be run on a continuous basis, using $CF_4$ in the input stream, for up to 3 days at a time. The Applicant has also found that the process of the invention can produce TFE at a production rate of more than 100 g/h at an energy input rate of less than 20 kWh/kg TFE produced.

It is an advantage of the invention that the method and installation can utilise waste PTFE together with other fluorocarbon compounds as an input feed material. This, in turn, allows the installation of the invention to operate with little or no effluent waste being produced.

The Applicant has found that the method and the installation of the invention can be controlled within accurate parameters by the controlled addition of carbon.

We claim:

1. A method for producing a fluorocarbon compound, the method comprising the steps of:
   (a) generating, in a high temperature zone, an electrical arc between at least one pair of essentially non-consumable electrodes;
   (b) feeding into the high temperature zone at least one input material with which to generate a thermal plasma having fluorine-containing species and carbon-containing species;
   (c) generating, in the high temperature zone, the thermal plasma having fluorine-containing species and carbon-containing species;
   (d) providing a particulate carbon-containing substance;
   (e) mixing, under controlled enthalpy conditions, the particulate carbon-containing substance with the thermal plasma to form a reactive thermal mixture thereof having molar C:F ratio between about 0.4 and 2, the reactive thermal mixture having a specific enthalpy between about 1 kWh/kg and about 10 kWh/kg;
   (f) controlling said specific enthalpy for a time interval to cause the reactive thermal mixture to be gaseous, the reactive thermal gaseous mixture containing reactive species including reactive fluorine-containing precursors and reactive carbon-containing precursors, said precursors being derived from the fluorine-containing species, the carbon-containing species, and the particulate carbon-containing substance; and
   (g) cooling the reactive thermal gaseous mixture at a cooling rate and to a cooling temperature selected to produce an end product including the fluorocarbon compound.

2. A method as claimed in claim 1, wherein the input material is an input gas stream and includes at least one fluorocarbon compound in the form of a short chain perfluorinated carbon compound of the general formula $C_nF_m$, in which $0<n\leq 10$, and m is selected from the group consisting of 2n, 2n+2 and 2n−2 where n>1.

3. A method as claimed in claim 2, in which the input material includes at least one gaseous fluorocarbon compound selected from the group consisting of difluoroethyne ($C_2F_2$), tetrafluoroethylene ($C_2F_4$), hexafluoroethane ($C_2F_6$), hexafluoropropene ($C_3F_6$), octafluoropropane ($C_3F_8$), tetrafluoromethane ($CF_4$), octafluorobutene ($C_4F_8$), and decafluorobutane ($C_4F_{10}$).

4. A method as claimed in claim 2, wherein the input gas stream includes fluorine gas, the fluorine gas being present in an amount between about 5 and 30 mol % of the input gas.

5. A method as claimed in claim 1, further comprising the step of preheating the particulate carbon-containing substance prior to step (e), said mixing is accomplished by introducing the particulate carbon-containing substance in step (e) into the plasma at a rate and a temperature, the rate and temperature being controlled so that the carbon-containing particles reach temperatures between about 2000 K. and 3000 K. in the reactive thermal mixture.

6. A method as claimed in claim 1, wherein the particulate carbon-containing substance is particulate carbon with a particle size from about $10^{-3}$ mm to about 0.3 mm, and wherein the carbon is essentially free of hydrogen, silicon, and sulphur.

7. A method as claimed in claim 1, wherein the particulate carbon-containing substance includes particulate polytetrafluoroethylene.

8. A method as claimed in claim 1, the method further comprising the step of providing a mixing zone adjacent the high temperature zone, the mixing of step (e) occurring in the mixing zone, the mixing zone being maintained at a pressure of about 0.01 to 1.0 bar.

9. A method as claimed in claim 1, wherein the end product further includes unreacted solid carbon-containing particles, the method further comprising the steps of:

separating the unreacted solid carbon-containing particles from the end product; and recycling the separated carbon-containing particles for mixing again in step (e).

10. A method as claimed in claim 1, wherein the cooling of step (g) takes place within selected parameters, the parameters being a selected cooling period and a selected range of cooled temperatures, the cooled thermal mixture being maintained within the selected range of cooled temperatures for a selected time period, each parameter being selected to determine the fluorocarbon compound of the end product.

11. A method as claimed in claim 10, wherein the cooling of step (g) occurs at a cooling rate of between 500 to $10^8$ K/s, the selected range of cooled temperatures being between about 100 K. and about 1200 K., the end product including at least one fluorocarbon compound selected from the group consisting of tetrafluoroethylene ($C_2F_4$ or TFE), hexafluoroethane ($C_2F_6$), hexafluoropropene ($C_3F_6$), octafluoropropane ($C_3F_8$), and tetrafluoromethane ($CF_4$ or carbon tetrafluoride).

12. A method as claimed in claim 10, wherein the reactive thermal mixture in step (g) is cooled from the specific enthalpy of between about 2 kWh/kg and 3 kWh/kg to the selected range of cooled temperatures in less than about 0.05 seconds, the selected range of cooled temperatures being below about 800 K., the cooled thermal mixture being maintained within the selected range of cooled temperatures for a time period of at least about 0.01 seconds, to produce tetrafluoroethylene as the fluorocarbon compound of the end product.

13. A method as claimed in claim 10, wherein the reactive thermal mixture in step (g) is cooled from the specific enthalpy of between about 2 kWh/kg and 3 kWh/kg to the selected range of cooled temperatures in less than about 0.5 to 3 seconds, the selected range of cooled temperatures being between about 800 K. and 1100 K., the cooled thermal mixture being maintained within the selected range of cooled temperatures for a time period of at least about 0.01 seconds, to produce hexafluoropropene as the fluorocarbon compound of the end product.

14. A method as claimed in claim 1, wherein the essentially non-consumable electrodes are provided by a plasma burner, the electrodes comprising an anode and a cathode selected from the group consisting of copper, nickel, and copper/nickel alloy electrodes, each electrode optionally having an insert selected from the group consisting of graphite and doped graphite, the electrodes being cooled to and maintained at a temperature below about 1300 K.

15. A method as claimed in claim 14, in which the anode consists of copper or a copper alloy and is cooled to and maintained at the temperature below about 1300 K., and the cathode consists of copper or a copper alloy with an insert selected from the group consisting of graphite or doped graphite and is intensely cooled to and maintained at a temperature below about 800 K.

16. A method as claimed in claim 14, further comprising the step of generating a vortex in the plasma.

17. A method for producing a fluorocarbon compound, the method comprising the steps of:

(a) providing a high temperature zone by providing an electrical arc between essentially non-consumable electrodes;

(b) providing a mixing zone adjacent the high temperature zone;

(c) feeding an input gas stream containing at least one fluorocarbon substance into the high temperature zone and generating a thermal plasma in the high temperature zone, the thermal plasma having fluorine-containing species and carbon-containing species, the thermal plasma having a molar C:F ratio, x, and a specific enthalpy, y;

(d) controlling the molar C:F ratio, x in the thermal plasma at a selected value between about 0.4 and 2;

(e) controlling in the high temperature zone the specific enthalpy, y, of the thermal plasma between about 1 kWh/kg and about 10 kWh/kg;

(f) introducing a particulate carbon-containing substance into the mixing zone to mix with the thermal plasma while maintaining the C:F ratio at the selected value to form a reactive thermal mixture in which the carbon-containing particles reach temperatures of between about 2000 K. and 3000 K., the reactive thermal mixture having reactive species including reactive fluorine-containing precursors and reactive carbon-containing precursors, the reactive thermal mixture having a specific enthalpy of not less than about 3 kWh/kg;

(g) maintaining the reactive thermal mixture at the conditions defined in step (f) for a time interval; and (h) rapidly cooling the reactive thermal mixture in a cooling zone in a manner to produce a product mixture having at least one fluorocarbon compound.

18. A method as claimed in claim 17, wherein the essentially non-consumable electrodes are provided by a plasma burner, the electrodes comprising an anode and a cathode selected from the group consisting of copper, nickel, and copper/nickel alloy electrodes, each electrode optionally having an insert selected from the group consisting of graphite and doped graphite, the electrodes being cooled to and maintained at a temperature below about 1200 K., the high temperature zone being located in and around the arc of each plasma burner, the mixing zone being located in an area of a tail flame of the burner.

19. An installation for producing fluorocarbon compounds, the installation comprising:

(a) a high temperature zone suitable for containing a thermal plasma;

(b) a pair of essentially non-consumable electrodes for creating an electrical area in the high temperature zone for converting an input material fed into the zone into a thermal plasma, the thermal plasma having fluorine-containing species and carbon-containing species;

(c) an input material feed means for introducing an input material into the high temperature zone;

(d) a mixing zone for allowing the thermal plasma to mix with a particulate material to form a reactive thermal mixture;

(e) a particulate material introduction means for introducing under controlled enthalpy conditions a particulate carbon-containing substance into the mixing zone to form the reactive thermal mixture, the reactive thermal mixture containing reactive species including reactive fluorine-containing precursors and reactive carbon-containing precursors;

(f) a reaction zone means for permitting the reactive thermal mixture to form a reactive thermal gaseous mixture under controlled enthalpy conditions and with a controlled C:F ratio, the reactive thermal gaseous mixture containing reactive species including reactive fluorine-containing precursors and reactive carbon-containing precursors;

(g) a control means for controlling specific enthalpy and the C:F ratio in the reactive thermal mixture; and (h) a cooling means for cooling the reactive thermal mixture in a controlled manner to produce an end product containing at least one specified fluorocarbon compound.

20. An installation as claimed in claim 19, wherein the essentially non-consumable electrodes are provided in a plasma burner, the electrodes being selected from the group consisting of copper, nickel, and copper/nickel alloy electrodes, each electrode optionally having an insert selected from the group consisting of graphite and doped graphite, the installation further comprising a cooling means being for cooling the electrodes to and maintaining them at a temperature below about 1300 K.

21. An installation as claimed in claim 20, in which the anode consists of copper or a copper alloy and is cooled to and maintained at the temperature below about 1300 K., and the cathode consists of copper or a copper alloy with a graphite insert and is intensely cooled to and maintained at a temperature below about 800 K.

22. An installation as claimed in claim 20, the plasma burner further comprising a vortex generator for generating a vortex in the thermal plasma in the high temperature zone.

23. An installation as claimed in claim 20, wherein the installation has three plasma burners with exit ports where tail flames are formed when the plasma burners are used, the plasma burners being arranged with their exit ports directed into a mixing chamber so that the tail flames extend into the mixing chamber to form the mixing zone in the mixing chamber when the plasma burners are used.

24. An installation as claimed in claim 19, wherein the particulate material introduction means comprises a hopper capable of delivering to the mixing zone particulate material having a particle size from about $10^{-3}$ mm to about 0.3 mm, the installation further comprising a heating means between the hopper and the mixing zone for heating the particulate carbon-containing substance before the particulate carbon-containing substance enters the mixing zone.

\* \* \* \* \*